United States Patent
Lentz et al.

(10) Patent No.: US 10,316,199 B2
(45) Date of Patent: *Jun. 11, 2019

(54) CAPSULES HAVING SURFACTANT TETHERED OUTER SHELLS AND METHODS FOR MAKING SAME

(71) Applicant: Microtek Laboratories Inc., Dayton, OH (US)

(72) Inventors: Carl M Lentz, Waynesville, OH (US); Kayla L. M. Ryan, Fairborn, OH (US)

(73) Assignee: Microtek Laboratories Inc., Dayton, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/646,421

(22) Filed: Jul. 11, 2017

(65) Prior Publication Data

US 2018/0009996 A1    Jan. 11, 2018

Related U.S. Application Data

(60) Provisional application No. 62/360,672, filed on Jul. 11, 2016, provisional application No. 62/419,325, filed on Nov. 8, 2016.

(51) Int. Cl.
   *C09D 5/14*   (2006.01)
   *C09D 179/04*   (2006.01)
   (Continued)

(52) U.S. Cl.
   CPC ............ *C09D 5/14* (2013.01); *A01N 25/28* (2013.01); *A01N 59/06* (2013.01); *A01N 59/16* (2013.01);
   (Continued)

(58) Field of Classification Search
   None
   See application file for complete search history.

(56) References Cited

U.S. PATENT DOCUMENTS 6,207,738 B1   3/2001   Zuckerman et al.
6,503,976 B2   1/2003   Zuckerman et al.
(Continued)

FOREIGN PATENT DOCUMENTS

WO   2003055588 A1   10/2003
WO   2015157354 A1   10/2015
WO   2015158003 A1   10/2015

OTHER PUBLICATIONS

International Search Report and Written Opinion dated Sep. 29, 2017, in PCT/US2017/041502, Applicant Microtek Laboratories, Inc. (10 pages).
(Continued)

*Primary Examiner* — Joseph D Anthony
(74) *Attorney, Agent, or Firm* — FisherBroyles, LLP; Susan M. Oiler

(57) ABSTRACT

Microcapsules are disclosed that have a core composition encapsulated within a polymer wall, and an inorganic shell connected to an exterior surface of the polymer wall by a surfactant. The inorganic shell has a cation attracted to the surfactant and an anion or anion equivalent chemically bonded to the cation to form the shell or has the metal portion of a metal-containing compound attracted to the surfactant to form the shell. The shell may comprise a Ca, Mg, or Ag metal compound. The shell may be a graphene oxide-metal compound.

36 Claims, 9 Drawing Sheets

Shell Formation

Shell Formation

(51) Int. Cl.

| | | |
|---|---|---|
| C09D 161/28 | (2006.01) | |
| C09D 133/00 | (2006.01) | |
| A01N 59/26 | (2006.01) | |
| A01N 59/20 | (2006.01) | |
| A01N 25/28 | (2006.01) | |
| A01N 59/06 | (2006.01) | |
| A01N 59/16 | (2006.01) | |
| B01J 13/22 | (2006.01) | |
| C09K 5/06 | (2006.01) | |
| B01J 13/08 | (2006.01) | |
| C09D 5/00 | (2006.01) | |
| C09F 9/00 | (2006.01) | |
| B01J 13/02 | (2006.01) | |
| B01J 13/14 | (2006.01) | |
| F28D 20/02 | (2006.01) | |
| C09D 7/61 | (2018.01) | |
| C09D 7/40 | (2018.01) | |
| C09D 161/34 | (2006.01) | |
| C08G 14/08 | (2006.01) | |

(52) U.S. Cl.
CPC .............. A01N 59/20 (2013.01); A01N 59/26 (2013.01); B01J 13/02 (2013.01); B01J 13/08 (2013.01); B01J 13/14 (2013.01); B01J 13/22 (2013.01); C09D 5/00 (2013.01); C09D 7/61 (2018.01); C09D 7/66 (2018.01); C09D 133/00 (2013.01); C09D 161/28 (2013.01); C09D 161/34 (2013.01); C09D 179/04 (2013.01); C09F 9/00 (2013.01); C09K 5/063 (2013.01); F28D 20/023 (2013.01); C08G 14/08 (2013.01); Y02E 60/145 (2013.01)

(56) References Cited

U.S. PATENT DOCUMENTS

| | | | |
|---|---|---|---|
| 6,514,362 | B1 | 2/2003 | Zuckerman et al. |
| 7,377,968 | B2 | 5/2008 | Reybuck et al. |
| 7,919,184 | B2 | 4/2011 | Mohapatra et al. |
| 7,938,897 | B2 | 5/2011 | Hart et al. |
| 2008/0272332 | A1* | 11/2008 | Joseph .................. A61K 8/0208 252/70 |
| 2009/0278074 | A1* | 11/2009 | Cox .......................... D01F 1/10 252/67 |
| 2010/0087115 | A1* | 4/2010 | Davis ....................... B01J 13/22 442/136 |
| 2010/0297446 | A1 | 11/2010 | Oxley et al. |
| 2013/0228308 | A1* | 9/2013 | Abhari ................... C09K 5/063 165/104.17 |
| 2014/0023853 | A1* | 1/2014 | Gueret .................... B01D 53/02 428/323 |
| 2014/0043754 | A1 | 2/2014 | Hartmann et al. |
| 2014/0197355 | A1 | 7/2014 | Ram et al. |
| 2015/0158003 | A1 | 6/2015 | Virgallito et al. |
| 2015/0190774 | A1* | 7/2015 | Phipps ..................... A01N 25/28 427/213.34 |
| 2018/0010013 | A1* | 1/2018 | Lentz ........................ C09F 9/00 |

OTHER PUBLICATIONS

Yu et al., "Microencapsulation of n-octadecane phase change material with calcium carbonate shell for enhancement of thermal conductivity and serving durability: Synthesis, microstructure, and performance evaluation", Applied Energy, 114 (2014) 632-643.
Boehm et al., "Graphite Oxide and Its Membrane Properties", J. Chim. Phys., 58 (1961) 141-147.
Cao et al., "Properties evaluation and applications of thermal energystorage materials in buildings", Renewable and Sustainable Energy Reviews, vol. 48, Aug. 2015, pp. 500-522.
Dreyer et al., "The chemistry of graphene oxide", Chem Soc Rev. Jan. 2010;39(1):228-40. doi: 10.1039/b917103g. Epub Nov. 3, 2009.
Ge et al., "Stability and optimum polymerized condition of polysiloxane—polyacrylate core/shell polymer", Advances in Polymer Technology, vol. 29, Issue 3, 161-172, 2010, Abstract only.
Gray et al., "Determination of microcapsule physicochemical, structural, and mechanical properties", Particuology, vol. 24, 2016, pp. 32-43, Abstract only.
He et al., "New approach for sol-gel synthesis of microencapsulated n-octadecane phase change material with silica wall using sodium silicate precursor", Energy, 67:223-233, 2014 Abstract only.
Kamdem et al., "Optimization Process by Complex Coacervation of Fish Oil Using Gelatin/SDS/NaCMC and Secondary Coating Application with Sodium Polyphosphate", IJSBAR. 2014, 17(1):74-94.
Liao et al., "Preparation of Organic/Inorganic Hybrid Polymer Emulsions with High Silicon Content and Sol-gel-derived Thin Films", Chinese Journal of Chemical Engineering, 18(1):156-163, 2010 Abstract only.
Long et al., "Organic-inorganic double shell composite microcapsules", Chemical Communications, 46:1718-1720, 2010.
Mondal, "Phase change materials for smart textiles—An overview", Applied Thermal Engineering, vol. 28, Issues 11-12, Aug. 2008, pp. 1536-1550.
Nelson, "Application of microencapsulation in textiles", Int J Pharm. Aug. 21, 2002;242(1-2):55-62.
Nomura, "Microencapsulation of Metal-based Phase Change Material for High-temperature Thermal Energy Storage", Scientific Reports, 5:9117, DOI:10.1038/srep09117.
Onder et al., "Encapsulation of Phase Change Materials by Complex Coacervation to Improve Thermal Performances of Woven Fabrics", Thermochimica Acta. 2008, 467, 63-72 Abstract only.
Pan et al., "Preparation, characterization and thermal properties of micro-encapsulated phase change materials", Solar Energy Materials and Solar Cells, 98:66-70, 2012.
Wang et al., "Highly efficient and selective infrared absorption material based on layered double hydroxides for use in agricultural plastic film" Applied Clay Science. 53(4):592-597, 2011, Abstract only.
Yavari et al., "Enhanced Thermal Conductivity in a Nanostructured Phase Change Composite due to Low concentration Graphene Additives", J. Phys. Chem. C, 2011, 115 (17), pp. 8753-8758, Abstract only.
Yu et al., "Self-Assembly Synthesis of Microencapsulated n-Eicosane Phase-Change Materials with Crystalline-Phase-Controllable Calcium Carbonate Shell", Energy Fuels, 2014, 28 (5), pp. 3519-3529, Abstract only.
Yu et al., "Microencapsulation of n-octadecane phase change material with calcium carbonate shell for enhancement of thermal conductivity and serving durability: Synthesis, microstructure, and performance evaluation", Applied Energy, 114:632-643, 2014, Abstract only.
Zhang et al., "Design and fabrication of dual-functional microcapsules containing phase change material core and zirconium oxide shell with fluorescent characteristics", Solar Energy Materials and Solar Cells, 133:56-68, 2015, Abstract only.

* cited by examiner

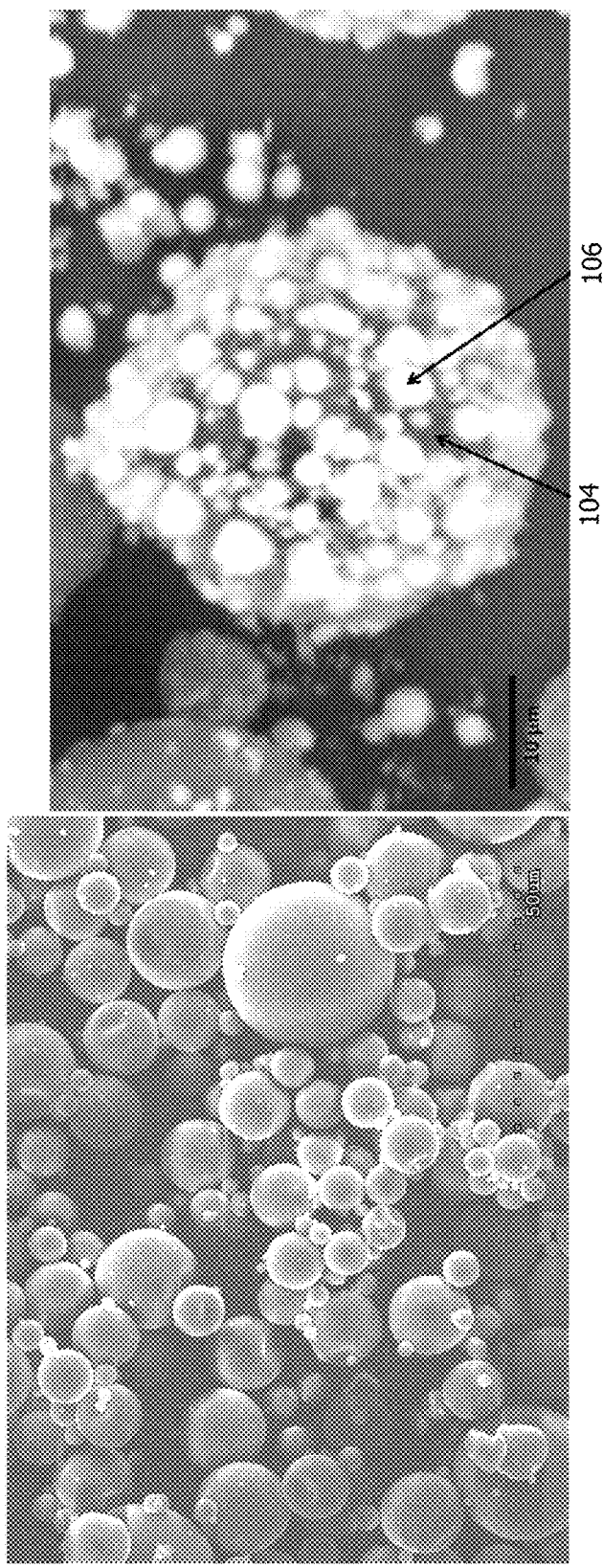

CAPSULES HAVING SURFACTANT TETHERED OUTER SHELLS AND METHODS FOR MAKING SAME

RELATED APPLICATIONS

This application claims the benefit of U.S. Provisional Application No. 62/360,672, filed Jul. 11, 2016, which is incorporated herein by reference, and the benefit of U.S. Provisional Application No. 62/419,325, filed Nov. 8, 2016, which is incorporated herein by reference.

TECHNICAL FIELD

The present application relates to capsules having a polymer wall encapsulating a core composition with a surfactant tethering an outer shell to the polymer wall, more particularly, the outer shell is precipitated as a solid comprising a metal cation bonded to the surfactant.

BACKGROUND

Microcapsules can be constructed of various types of wall or shell materials to house varying core material for many purposes. The encapsulation process is commonly referred to as microencapsulation. Microencapsulation is the process of surrounding or enveloping one substance, often referred to as the core material, within another substance, often referred to as the wall, shell, or capsule, on a very small scale. The scale for microcapsules may be particles with diameters in the range between 1 and 1000 μm that consist of a core material and a covering shell. The microcapsules may be spherically shaped, with a continuous wall surrounding the core, while others may be asymmetrical and variably shaped.

General encapsulation processes include emulsion polymerization, bulk polymerization, solution polymerization, and/or suspension polymerization and typically include a catalyst. Emulsion polymerization occurs in a water/oil or oil/water mixed phase. Bulk polymerization is carried out in the absence of solvent. Solution polymerization is carried out in a solvent in which both the monomer and subsequent polymer are soluble. Suspension polymerization is carried out in the presence of a solvent (usually water) in which the monomer is insoluble and in which it is suspended by agitation. To prevent the droplets of monomers from coalescing and to prevent the polymer from coagulating, protective colloids are typically added.

Through a selection of the core and shell material, it is possible to obtain microcapsules with a variety of functions. This is why microcapsules can be defined as containers, which can release, protect and/or mask various kinds of active core materials. Microencapsulation is mainly used for the separation of the core material from the environment, but it can also be used for controlled release of core material in the environment.

Microencapsulation has attracted a large interest in the field of phase change materials (PCMs). A PCM is a substance with a high heat of fusion, melting and solidifying at a certain temperature, which is capable of storing and releasing large amounts of energy. Heat is absorbed or released when the material changes from solid to liquid and vice versa; thus, PCMs are classified as latent heat storage units. The latent heat storage can be achieved through solid-solid, solid-liquid, solid-gas and liquid-gas phase change, but solid-liquid is typically used in thermal storage applications as being more stable than gas phase changes as a result of the significant changes in volume occupied by the PCM. Because of this ability, PCMs are currently being used in a wide variety of fields including textiles, food and medical industries, computer cooling, spacecraft thermal systems, and solar power plants. Generally, the most commonly used PCMs in use today are those made from paraffin waxes. Additionally, because PCMs transition from solid to liquid when heated past the melting point, paraffin waxes are most easily handled when encapsulated, with the most common outer wall being an organic polymer. This allows PCMs to be handled as free-flowing solids past the melting temperature of the PCM, and the organic polymer wall improves controlled release of the PCM, if that is desired, and structural stability of the capsule.

Some disadvantages exist in current organic polymer wall systems of the microencapsulated PCMS, including flammability (too high), low far infrared (FIR) absorption, little to no defense against bacterial and fungal growth, and low thermal conductivity. Previously, to combat these limitations, researchers have tried direct encapsulation of PCMs with inorganic walls, such as calcium carbonate ($CaCO_3$), silica, aluminum hydroxide ($Al(OH)_3$), and oxides of metals such as Mg, Ca, Ti, and Zn, but the walls have been ineffective at containing the PCM. In particular, a major issue with this type of direct encapsulation is the amount of PCM that leaks from the capsule, as much as 30% leakage. Leakage of the PCM in such quantities, especially when the PCM is a paraffin wax, could increase the flammability of the microcapsules. Furthermore, in order to obtain a complete wall of inorganic material encapsulating the paraffin core, a mass ratio of around 40/60 (wax core/wall) must be used. This high mass ratio causes a nearly 60% loss in enthalpy, which significantly lowers the ability to effectively use the PCM core for many of the applications mentioned above. Therefore, wall materials are limited to organic polymers.

Some further potential applications of PCMs include heating/cooling systems in buildings as well as solar energy storage. Efficient heating and cooling systems in buildings have come a long way in recent years; however, there is still room for improvement. Because of PCMs' ability to store and release heat when needed, PCMs have applications in heating/cooling systems in buildings. However, due to the flammability of organic PCMs, the applications are limited. Additionally, solar panels are becoming much more efficient at energy conversion; however, a method of storage of this energy for later use is needed. Energy is released in the form of FIR light from the sun, and radiates both during day and night. Because of this, a material that is able to absorb FIR energy and store it as heat would be desirable in solar energy applications. PCMs have the ability to store and release heat over longer periods of time.

Since the development of microencapsulated PCMs, there has been a constant need for improved microcapsules. In particular, there is a need to find a way to use inorganic materials as walls of microcapsules in a way to get the benefits of the inorganic material without leakage of the core and without decreasing the heat of fusion of the microcapsule.

SUMMARY

Disclosed herein are capsules having an outer shell, in particular an inorganic material, tethered to a polymer wall of a capsule, which may be a microcapsule, by a surfactant and methods of making the same. The outer shell minimizes the loss in enthalpy and minimizes the leakage of the core composition, while providing beneficial characteristics to the capsule attributed to the material used in the outer shell. For example, if the outer shell comprises $CaCO_3$, improved flame retardant properties are a characteristic of the capsules. If the outer shell comprises $CaHPO_4$ and/or $CaSO_3$, increased absorption of far infrared light is a characteristic of the capsules. If the outer shell comprises one or more silver compounds, high resistivity against bacteria is a characteristic of the capsules. If the outer shell comprises a calcium graphene oxide compound, high thermal conductivity is a characteristic of the microcapsule.

In all aspects, the capsules have a core composition encapsulated within a polymer wall, and an inorganic shell connected to an exterior surface of the polymer wall by a surfactant, the inorganic shell comprising a cation attracted to the surfactant and an anion or anion equivalent chemically bonded to the cation or a metal-containing compound attracted to the surfactant. The surfactant comprises an ionic surfactant.

In all aspects, the core comprises a phase change material. The cation may be calcium ions, silver ions, magnesium ions, iron ions, copper ions, and cobalt ions, and combinations thereof. When the cation is a silver ion, the inorganic shell has antibacterial and antifungal growth properties.

In all aspects, the core comprises a phase change material. The cation may be calcium ions, silver ions, magnesium ions, iron ions, copper ions, and cobalt ions, and combinations thereof. In one embodiment, the inorganic shell provides the capsule with a flame retardant property that reduces the percent of total mass burned, compared to the capsule without the shell, by at least 16% mass. In another embodiment, the inorganic shell provides the capsule with a flame retardant property that reduces the percent of total mass burned by at least 40%.

In all aspects, the core comprises a phase change material. The inorganic shell is defined by a cation and an anion, with the anion selected from $CO_3^{-2}$, $HPO_4^{-2}$, $PO_4^{-2}$, $SO_3^{-2}$, $OH^{-1}$, $HSO_4^{-1}$, and combinations thereof.

In one embodiment, the core comprises a phase change material and the inorganic shell is defined by a cation and an anion equivalent. The anion equivalent is graphene oxide and the cation is calcium ions. Here, the inorganic shell may be a discontinuous wall or a continuous wall.

In one embodiment, the core comprises a phase change material and the inorganic shell is defined by a metal-containing compound attracted to the surfactant, the metal-containing compound being a metal oxide or a metal oxide-hydroxide.

In all aspects, the polymer wall of the capsules comprises melamine formaldehyde, gelatin, cross-linked melamine, resorcinol urea formaldehyde, or acrylic polymer.

In another aspect, methods for surface treating capsules are disclosed. The method includes providing capsules comprising a core composition encapsulated within a polymer wall, mixing an aqueous surfactant comprising an ionic surfactant and the capsules together under conditions that enable the surfactant to attach to an exterior surface of the polymer wall to form a surfactant-capsule intermediate, and adding a metal-containing compound suspended, solubilized, or dissolved in water to the surfactant-capsule intermediate to form an inorganic solid as an outer shell of the capsules or firstly adding aqueous cations to the surfactant-capsule intermediate to form secondary intermediate capsules with the cations associated with the surfactant and then adding aqueous anions or anion equivalents to the secondary intermediate capsules to chemically bond to the cation and form an inorganic solid as an outer shell of the capsules.

The method may additionally include forming the capsules before mixing with the aqueous surfactant.

In all aspects of the methods, the shell may be a discontinuous outer shell and the core may be a phase change material. In one embodiment, the cation is selected from calcium ions, silver ions, magnesium ions, and combinations thereof and the anion is selected from $CO_3^{-2}$, $HPO_4^{-2}$, $PO_4^{-3}$, $SO_4^{-2}$, $SO_3^{-2}$, $OH^{-1}$, $HSO_4^{-1}$, and combinations thereof.

In all aspects of the methods, the shell may be a discontinuous outer shell and the core may be a phase change material. In one embodiment, the shell comprises a cation and an anion equivalent, which may be graphene oxide.

In all aspects of the methods, the shell may be a discontinuous outer shell and the core may be a phase change material. In one embodiment, the metal-containing compound was added during the adding step, and the metal-containing compound includes a metal oxide or a metal oxide-hydroxide.

In all aspects of the methods, the shell may be a discontinuous outer shell and the core may be a phase change material. The polymer wall comprises melamine formaldehyde, gelatin, cross-linked melamine, resorcinol urea formaldehyde, or acrylic polymer.

In another aspect articles of manufacture are disclosed that incorporate any of the above and below described capsules therein. In one aspect, the inorganic shell is defined by a cation and an anion equivalent, wherein the anion equivalent is graphene oxide, and the article of manufacture is a cooling apparatus for an electronic device. The cooling apparatus has a substrate with a coating applied thereto that comprises a plurality of the capsules dispersed therein. The substrate includes an adhesive layer on the substrate on a surface opposite the coating, and the inorganic shell comprises at least 1 g of graphene per microcapsule, and the microcapsules increase the average performance of the electronic device by at least 10%.

In one aspect, the core comprises a phase change material, and the cation is selected from calcium ions, silver ions, magnesium ions, iron ions, copper ions, and cobalt ions, and combinations thereof, and the capsule has a flame retardant property that reduces the percent of total mass burned, compared to the capsule without the shell, by at least 16% mass or at least 40%. Here, the article of manufacture may be a building material.

In another aspect, the article of manufacture is a solar cell, and the core of the capsules comprise a phase change material, and the inorganic shell comprises an anion selected from $HPO_4^{-2}$, $PO_4^{-3}$, $SO_4^{-2}$, $SO_3^{-2}$, $HSO_4^{-1}$, and combinations thereof.

In another aspect, the article of manufacture is a textile fabric or textile material. In one embodiment, the cation is a silver ion, and the inorganic shell has antibacterial and antifungal growth properties.

In another aspect, compositions of matter are disclosed the have a plurality of capsules dispersed with a spreadable medium. The plurality of capsules may be any of the capsules described herein. In one embodiment, the capsules having inorganic shells where the cation is a silver ion, thereby providing antibacterial and antifungal growth properties. In all aspects, the spreadable medium may be a paint or a coating.

BRIEF DESCRIPTION OF THE DRAWINGS

FIG. 2 is a Scanning Electron Microscope (SEM) image, 50 µm scale, of microcapsules having a core encapsulated by a polymer wall prior to the addition of an outer (exterior) shell, per the shell formation process of FIG. 1.

FIG. 3 is a SEM image, 10 µm scale, of a single microcapsule in the center of the frame having a $CaCO_3$ shell connected to an exterior surface of the polymer wall of a microcapsule of the type shown in FIG. 2.

DETAILED DESCRIPTION

The following detailed description will illustrate the general principles of the invention, examples of which are additionally illustrated in the accompanying drawings.

As used herein, the term "about" allows a degree of variability in a value or range, for example, within 10% of a stated value or of a stated limit of a range for all embodiments, but within 5% of a stated value or of a stated limit of a range in more preferred embodiments.

Figure 1A:
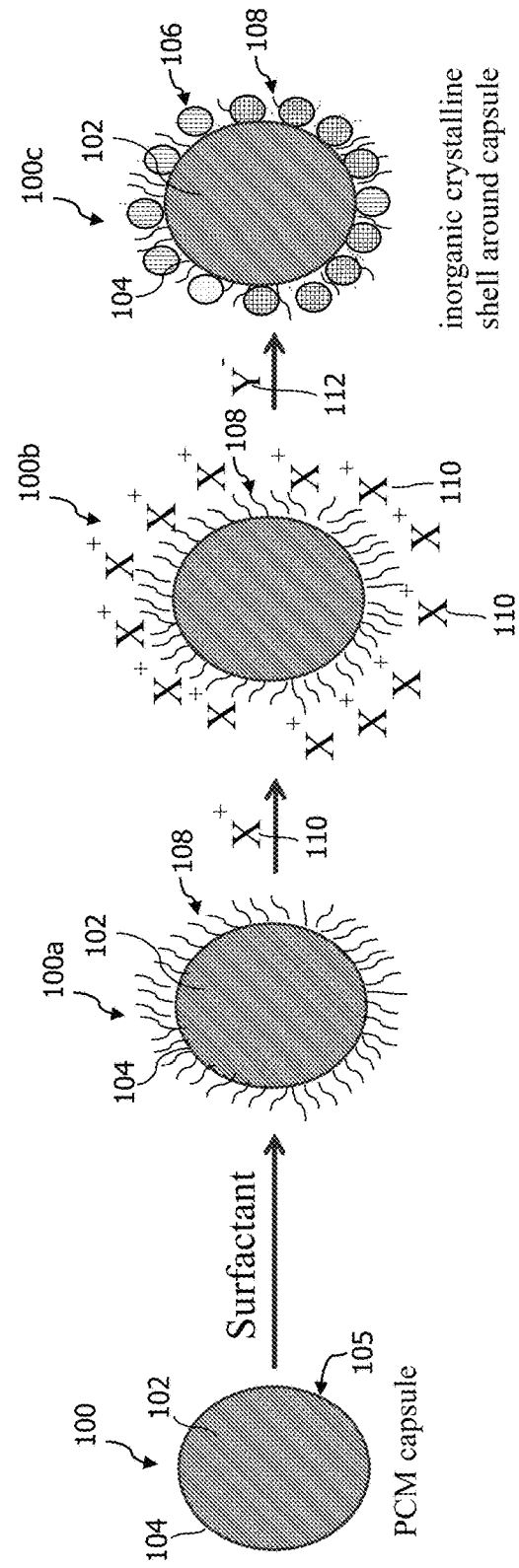
FIG. 1A is flow diagram of shell formation on microcapsules, represented as a cross-sectional view.
Figure 1B:
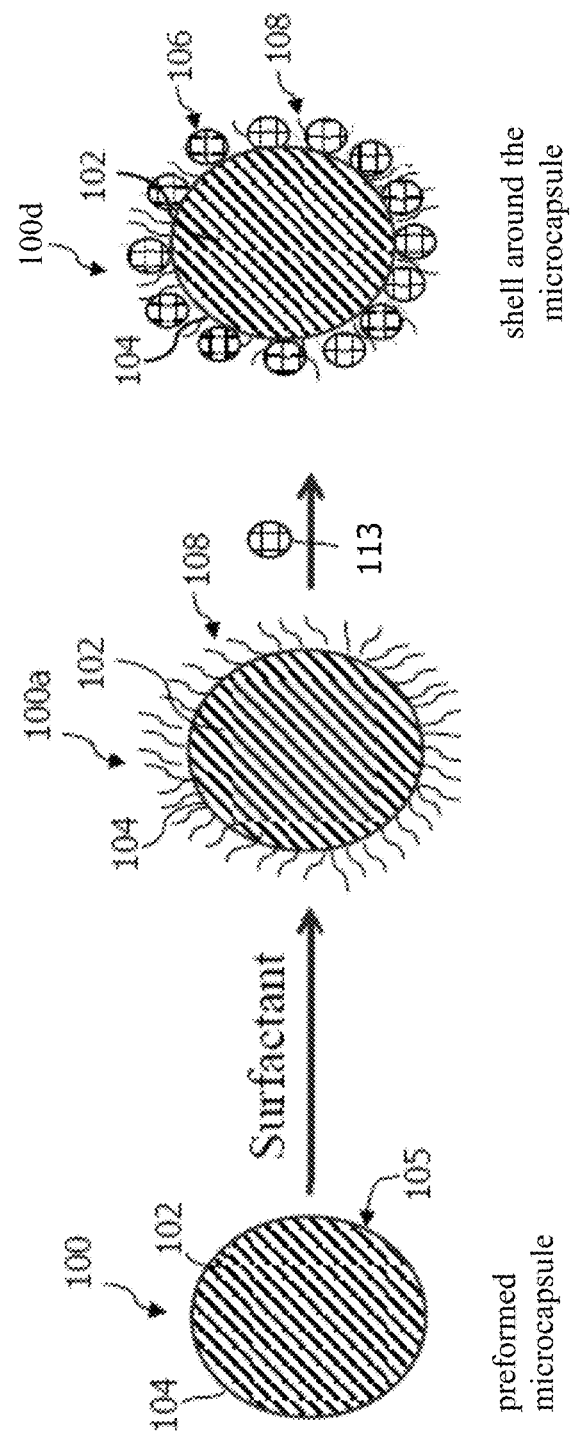
FIG. 1B is flow diagram of a second embodiment of shell formation on microcapsules, represented as a cross-sectional view.

Capsules 100c having an outer shell 106, an inorganic shell, surrounding a polymer wall 104 encapsulating a core composition 102 are described herein with reference to FIGS. 1A and 1B. The shell 106 is deposited onto the capsules, and is held in place by the surfactant. The shell 106 is typically an outermost shell, but in some embodiments the shell 106 may have a coating applied thereto. The capsules 100c begin as pre-formed capsules 100 that have a core composition 102 encapsulated within a polymer wall 104. An SEM image of one embodiment of pre-formed capsules is included as FIG. 2. It is noted that the capsules are generally spherical capsules and based on their size are referred to as microcapsules.

With reference to FIG. 1A, the shell 106 is connected to an exterior surface 105 of the polymer wall 104 of the pre-formed capsule 100 by a surfactant 108, and has a cation 110 attracted to the surfactant 108 and an anion or an anion equivalent 112 chemically bonded to the cation to form a solid precipitate (i.e., the shell 106). The surfactant 108 is chemically bonded to the exterior surface of the polymer wall by at least an electrostatic attraction or a hydrophobic association, and the cation forms a chemical bond with the surfactant. The shell 106 may be a continuous shell (i.e., a full, endless shell) or a discontinuous (partial) shell. Examples of a discontinuous shell are shown in the SEM images of FIGS. 3-5. The shell 106 is deposited onto the capsules, held there by the surfactant.

With reference to FIG. 1B, in an alternate process, the shell 106 is connected to an exterior surface 105 of the polymer wall 104 of the pre-formed capsule 100 by a surfactant 108, and has a metal-containing compounding 113 attracted to the surfactant 108 to form a solid shell 106. Here too, the surfactant 108 is chemically bonded to the exterior surface of the polymer wall by at least an electrostatic attraction or a hydrophobic association, with the difference being that the metal-portion of the metal-containing compound forms a chemical bond with the surfactant rather than a cation. The shell 106 may be a continuous shell or a discontinuous shell, as noted above. One example metal-containing compound is boehmite (an aluminum oxide hydroxide mineral) that may form a shell 106 about a capsule housing a core composition comprising a PCM. Other metal-containing compounds include, but are not limited to, titanium dioxide, silicon oxide, zinc oxide, copper oxide, zirconium oxide, and other metal oxides or metal oxide-hydroxide nanoparticles. The metal-containing compounds do not have to be soluble in water. Suspendability in water long enough to attach to the surfactant is all the is needed.

In all embodiments, the core composition 102 may include a phase change material, preferably one that has a melting point in a range of about −30° C. to about 70° C. PCMs with such melting points include, but are not limited to, straight chain alkanes, alcohols, organic acids, aliphatic acids containing at least 6 carbon atoms, and combinations thereof. Other suitable core materials include, but are not limited to, aliphatic hydrocarbyl compounds such as saturated or unsaturated $C_{10}$-$C_{40}$ hydrocarbons, which are branched or preferably linear; cyclic hydrocarbons; aromatic hydrocarbyl compounds; $C_1$-$C_{40}$-alkyl-substituted aromatic hydrocarbons; saturated or unsaturated $C_6$-$C_{30}$-fatty acids; fatty alcohols; $C_n$-alkyl esters; natural and synthetic waxes, and combinations thereof.

Examples of saturated or unsaturated $C_{10}$-$C_{40}$ hydrocarbons, which are branched or preferably linear, include, but are not limited to, n-tetradecane, n-pentadecane, n-hexadecane, n-heptadecane, n-octadecane, n-nonadecane, n-eicosane, n-heneicosane, n-docosane, n-tricosane, n-tetracosane, n-pentacosane, n-hexacosane, n-heptacosane, and n-octacosane. Examples of cyclic hydrocarbons include, but are not limited to, cyclohexane, cyclooctane, and cyclodecane. Examples of aromatic hydrocarbyl compounds include, but are not limited to, benzene, naphthalene, biphenyl, and o- or n-terphenyl. Examples of $C_1$-$C_{40}$-alkyl-substituted aromatic hydrocarbons include, but are not limited to, dodecylbenzene, tetradecylbenzene, hexadecylbenzene, hexylnaphthalene or decyinaphthalene. Examples of saturated or unsaturated $C_6$-$C_{30}$-fatty acids include, but are not limited to, lauric, stearic, oleic or behenic acid, and eutectic mixtures of decanoic acid with myristic, palmitic or lauric acid. Examples of fatty alcohols include, but are not limited to, lauryl, stearyl, oleyl, myristyl, cetyl alcohol, mixtures such as coconut fatty alcohol, and the so-called oxo alcohols which are obtained by hydroformylation of α-olefins and further reactions. Examples of $C_n$-alkyl esters include, but are not limited to, $C_1$-$C_{10}$-alkyl esters of fatty acids, such as propyl palmitate, methyl stearate or methyl palmitate, and their eutectic mixtures or methyl cinnamate. Examples of natural and synthetic waxes include, but are not limited to, montan acid waxes, montan ester waxes, polyethylene wax, oxidized waxes, polyvinyl ether wax, and ethylene vinyl acetate wax.

Since the core material is already encapsulated in the pre-formed capsules 100 (FIG. 1) and has no interaction with the formation of the additional shell 106 added by the methods disclosed herein, the core material 102 can be any desired composition capable of being encapsulated. The core composition and the material for the shell are selected based on an end application and desired additional property for the shell to contribute to the end product.

The pre-formed capsules 100 and the resultant capsules 100c can be microcapsules or macrocapsules, which will typically have a relatively high payload of the core material relative to the amount of material forming the shell and capsule wall. The payload of core material in any of the capsules may be about 10% to about 90% by weight based on the total weight of a capsule, preferably at least 50%, more preferably at least 70%, and even more preferably at least 80%. In any of the capsules made by the methods disclosed herein, the payload of core material may be about 70% to about 80% by weight, more preferably about 75% to about 85%, and even more preferably about 77% to about 81% by weight based on the total weight of a capsule.

The size of the resultant capsules 100c can vary depending upon the size of the pre-formed capsules 100 used and the amount of shell material deposited on the polymer wall 104 of the pre-formed capsules 100. The resultant capsules 100c can be microcapsules or macrocapsules. A microcapsule is typically one having a diameter in the range from about 1 µm to about 1000 µm. The capsule diameter selected depends upon a user's intended application or use for the capsules. For example, flavor capsules having diameters of 800 µm to 1200 µm are used in chewing gum products, whereas capsules having diameters of 30 µm to 1000 µm are used in construction for delivering phase change material, humidified or anti-fouling agents into concrete. In textiles, microcapsules having diameters of 1 µm to 500 µm are used for anti-allergic mattresses.

The pre-formed capsules 100 have a polymer wall 104, which may comprise melamine formaldehyde, gelatin, a cross-linked melamine, acrylic polymer, or other known wall material made using known methods such as in-situ polymerization, interfacial polycondensation, interfacial cross-linking, or any other known method. Melamine-formaldehyde (MF) capsules can be prepared by the in situ polymerization process of polycondensation, where the melamine-formaldehyde prepolymer is initially soluble in the continuous water phase, while a hydrophobic core material is contained in dispersed droplets. As the polymerization reaction starts in the aqueous solution, the formed oligomers start to collapse on the surface of the core droplets. On the surface, the polymerization continues and crosslinking occurs, which results in the formation of a solid MF wall.

Capsules having a gelatin wall encapsulating a core material are known, as taught in Onder et al. *Encapsulation of Phase Change Materials by Complex Coacervation to Improve Thermal Performances of Woven Fabrics*, Thermochimica Acta. 2008, 467, 63-72, and in Patrick et al. *Optimization Process by Complex Coacervation of Fish Oil Using Gelatin/SDS/NaCMC and Secondary Coating Application with Sodium Polyphosphate*, IJSBAR. 2014, 17, 74-94.

For a cross-linked melamine microcapsule, reference is made to co-pending U.S. application Ser. No. 15/420,435 for methods of making the microcapsule, which is incorporated herein by reference. These microcapsules are made from a melamine formaldehyde prepolymer comprising a crosslinking agent, the crosslinking agent being a mixture of:

(a) a reaction product of a cyclic urea (U) and a multifunctional aldehyde (A), and
(b) at least one crosslinker selected from the group consisting of (b1) reaction products of an aminotriazine and at least one aldehyde selected from the group consisting of aliphatic monoaldehydes and multifunctional aliphatic aldehydes having the structure $Y(CHO)_n$, where Y is an n-functional aliphatic residue, and n is greater than 1, where U is not dihydroxyethylene urea if the crosslinker (b) is (b1),
(b2) reaction products of urea and/or cyclic ureas and formaldehyde,
(b3) alkoxycarbonylaminotriazines,
(b4) multifunctional isocyanates which may be partially or completely blocked,
(b5) reaction products of phenols and aliphatic monoaldehydes,
(b6) multifunctional epoxides,
(b7) multifunctional aziridines,
(b8) multifunctional carbodiimides, wherein any of the crosslinkers (a) and (b) which have hydroxyl groups may be etherified with one or more linear, branched, or cyclic aliphatic alcohols, polymerized by adjusting the pH and/or addition of urea. The crosslinking agent (b) is preferably at least one crosslinker selected from the group consisting of (b1), (b2), (b3), and (b5). These cross-linked melamine microcapsules have MF prepolymer present in a ratio by weight percent to the crosslinking agent of 1:1 to 4:1, more preferably 1.5:1 to 3.75:1. These capsules have an initial free formaldehyde level of less than 100 ppm, more preferably less than 80 ppm, less than 60 ppm, and even more preferably less than 40 ppm. Such a crosslinking agent is available from Allnex USA Inc.

In one embodiment, the crosslinking agent has the reaction product of a cyclic urea U and a multifunctional aliphatic aldehyde A, portion (a), in a mixture with one or more of (b1), (b2), (b3) and (b5). Mixtures of the reaction product of a cyclic urea (U) and a multifunctional aldehyde (A) and at least one of the crosslinkers (b) have a ratio of the mass of the reaction product to the mass of the crosslinker (b) (or to the sum of the masses of all crosslinkers (b)) from 1/99 to 99/1, preferably from 10/90 to 90/10, and more preferably from 30/70 to 70/30.

The multifunctional aldehyde A has the formula OHC—R'—CHO where R' may be a direct bond or a divalent radical which may preferably be a linear, branched or cyclic aliphatic radical and may have from one to twenty carbon atoms, both these options for R' leading to a divalent aldehyde having exactly two —CHO groups, or an aliphatic divalent radical which may be linear, branched or cyclic and may have from one to twenty carbon atoms, which radical carries at least one additional aldehyde group —CHO, which latter option leads to trivalent or polyvalent aldehydes having at least three aldehyde groups. Preferred aldehydes are divalent aliphatic aldehydes, particularly glyoxal, malonic dialdehyde, succinic dialdehyde, and glutaric dialdehyde. Especially preferred is glyoxal in an aqueous solution, as anhydrous solid which has to be cooled as its melting temperature is 15° C., or in the form of its dimer or trimer, optionally in solid hydrated form as dihydrates, or in the form of its addition products with sulphites or hydrogen sulphites which decompose under acidic conditions.

The cyclic ureas U which may be used according to the present invention have at least one unsubstituted amidic —NH group. These cyclic ureas are cycloaliphatic or bicycloaliphatic compounds having an element of the structure —NH—CO—NH— within a ring structure, the total number of ring atoms preferably being from 5 to 7 (ethylene urea, 1,2-propylene urea, 1,3-propylene urea, 1,4-butylene urea or tetramethylene urea). Particularly preferred is ethylene urea or a mixture comprising ethylene urea, especially a mixture comprising at least a mass fraction of 50% of ethylene urea. In the case of a bicyclic compound, the simplest structure is glycoluril or acetylene diurea. Hydroxy functional ureas are not useful for the present invention. The cyclic ureas may be substituted, preferably by alkyl groups on the N- or C-atoms, or both, the alkyl residues preferably having from one to four carbon atoms. At least one of the nitrogen atoms must remain unsubstituted to enable reaction with the aldehyde functional molecule. Preferably, at least one cyclic urea is selected from the group consisting of ethylene urea, 1,2-propylene urea, hydantoin also known as glycolyl urea, and parabanic acid also known as oxalyl urea, and glycoluril. A particularly preferred combination is glyoxal reacted with ethylene urea, and optionally, either glyoxal, or ethylene urea, or both, in mixture with other multifunctional aldehydes and/or other cyclic ureas. In a preferred case of using ethylene urea as the cyclic urea, and glyoxal as the multifunctional aldehyde, —R'— is a direct bond, and —X— is —NH—CH$_2$—CH. Additional details are found in the co-pending application referenced above.

A melamine formaldehyde resin particularly suitable for the above cross-linked melamine capsules is CYMEL® 385 melamine formaldehyde resin available from Allnex USA Inc. The melamine formaldehyde resin may be one that includes phenol, such as a resorcinol urea formaldehyde resin.

One example method of making microcapsules that have an acrylic polymer wall is disclosed in U.S. Patent Application Publication No. 2015/0158003, published Jun. 11, 2015, which is incorporated herein by reference.

The surfactant 108 used to tether the shell 106 to the polymer wall 104 comprises an ionic surfactant. In one embodiment, the ionic surfactant may be mixed with a nonionic surfactant. The surfactant can affect the size and stability of the inorganic coated capsules as agglomeration can occur with some surfactant/shell system combinations and the stability of the shell. For example, an inorganic shell may detach from the polymer wall of the capsule 100 at a temperature of about 200° C. if it is not well bonded thereto. Most capsule walls are stable up to and about 300° C. to about 400° C.; thus, degradation at 200° C. is indicative that the surfactant is not tethering the metal to the polymer surface of the capsule.

Cationic surfactant can include, for example, amine salts, such as, ethoxylated tallow amine, cocoalkylamine, and oleylamine, quaternary ammonium compounds such as cetyl trimethyl ammonium bromide, myristyl trimethyl ammonium bromide, stearyl dimethyl benzyl ammonium chloride, lauryl/myristryl trimethyl ammonium methosulfate, stearyl octyldimonium methosulfate, dihydrogenated palmoylethyl hydroxyethylmonium methosulfate, isostearyl benzylimidonium chloride, cocoyl benzyl hydroxyethyl imidazolinium chloride, cocoyl hydroxyethylimidazolinium, or a mixture thereof. In some embodiments, the cationic surfactant is cetyl trimethyl ammonium bromide.

Suitable anionic surfactant include, but are not limited to, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate (SDBS), sodium dialkylsulfosuccinates, dioctyl sulfosuccinate, sodium dilaurylsulfosuccinate, poly(styrene sulfonates) and salts thereof, isobutylene-maleic anhydride copolymer, gum arabic, sodium alginate, carboxymethylcellulose, cellulose sulfate and pectin, isobutylene-maleic anhydride copolymer, carrageenan; semi-synthetic polymers such as sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropanesulfonic acid homopolymers and copolymers, and partial amide or partial ester of such polymers and copolymers, carboxymodified polyvinyl alcohol, sulfonic acid-modified polyvinyl alcohol and phosphoric acid-modified polyvinyl alcohol, phosphated or sulfated tristyrylphenol ethoxylates.

Example nonionic surfactants include, but are not limited to, ethylene maleic anhydride (EMA), sorbitan stearate (e.g., SPAN® 60), sorbitan monooleate (e.g., SPAN® 80), polyethylene glycol sorbitan monooleate (TWEEN® 80), polyvinyl alcohol, ethylene oxide/propylene oxide block copolymers (e.g., PLURONIC® P105), polyoxyethylene (5) nonylphenylether, branched (IGEPAL® CO-520), or a mixture thereof.

The cation 110 attracted to the surfactant 108 is a metal ion such as $Ca^{+2}$, $Mg^{+2}$, $Ag^{+1}$, $Co^{+2}$, $Co^{+3}$, $Ni^{+2}$, $Cu^{+1}$, $Cu^{+2}$, $Fe^{+2}$, $Fe^{+3}$, $Mn^{+2}$, $Zn^{+2}$, $Al^{+3}$, and $B^{+3}$, $Sn^{+2}$, $Sn^{+4}$, $Cr^{+2}$, $Cr^{+3}$, but is not limited thereto. The anion 112 for forming the shell 106 is one that is insoluble in water when paired with the cation 110. Suitable anions include, but are not limited to, one or more of $CO_3^{-2}$, $HPO_4^{-2}$, $PO_4^{-3}$, $SO_4^{-2}$, $SO_3^{-2}$, $OH^{-1}$, $H_2PO_4^{-1}$, $HSO_4^{-1}$, and $HSO_3^{-1}$, $CrO_4^{-2}$, $MnO_4^{-2}$, $S_2O_3^{-2}$. The anion equivalent is also insoluble in water when paired with the cation 110. Suitable anion equivalent includes graphene oxide, amines, and carboxylates. Some example amines include primary amines such as diethylenetriamine (DETA) and diethylamine (DEA). Some examples of carboxylates include octadecanoate ions, dodecanoate ions, and hexadecanoate ions.

In one embodiment, the capsules 100c have an inorganic shell 106 where the cation 110 is $Ca^{+2}$ and the anion is $CO_3^{-2}$. The calcium carbonate inorganic shell formed is a solid that may be continuous or discontinuous about the polymer wall 104. The scanning electron microscopy (SEM) image seen in FIG. 2 is an example of an organic PCM (capsule 100) having an exterior $CaCO_3$ inorganic shell via the procedure described herein. It can be seen from this image that in order to achieve a complete direct encapsulation (i.e., no polymer 104 being present) of a core composition, such as a phase change material, without severe leakage, much more calcium carbonate is needed. But, the more calcium carbonate on the surface of the capsule, the lower the heat of fusion of the capsule. Therefore, in order to prevent leakage, yet retain a high heat of fusion, the pre-formed capsule 100 (already encapsulated PCM) is used, where the polymer wall 104 contains the core without leakage. FIG. 2 also demonstrates the crystallization schematic of metal compounds, i.e., instead of forming a continuous wall, like a polymer, the metal compounds form rigid crystal lattices, where the shape is controlled by the coordination preferences of the metal, temperature at which the crystal forms, solvent, and pH.

Figure 7:
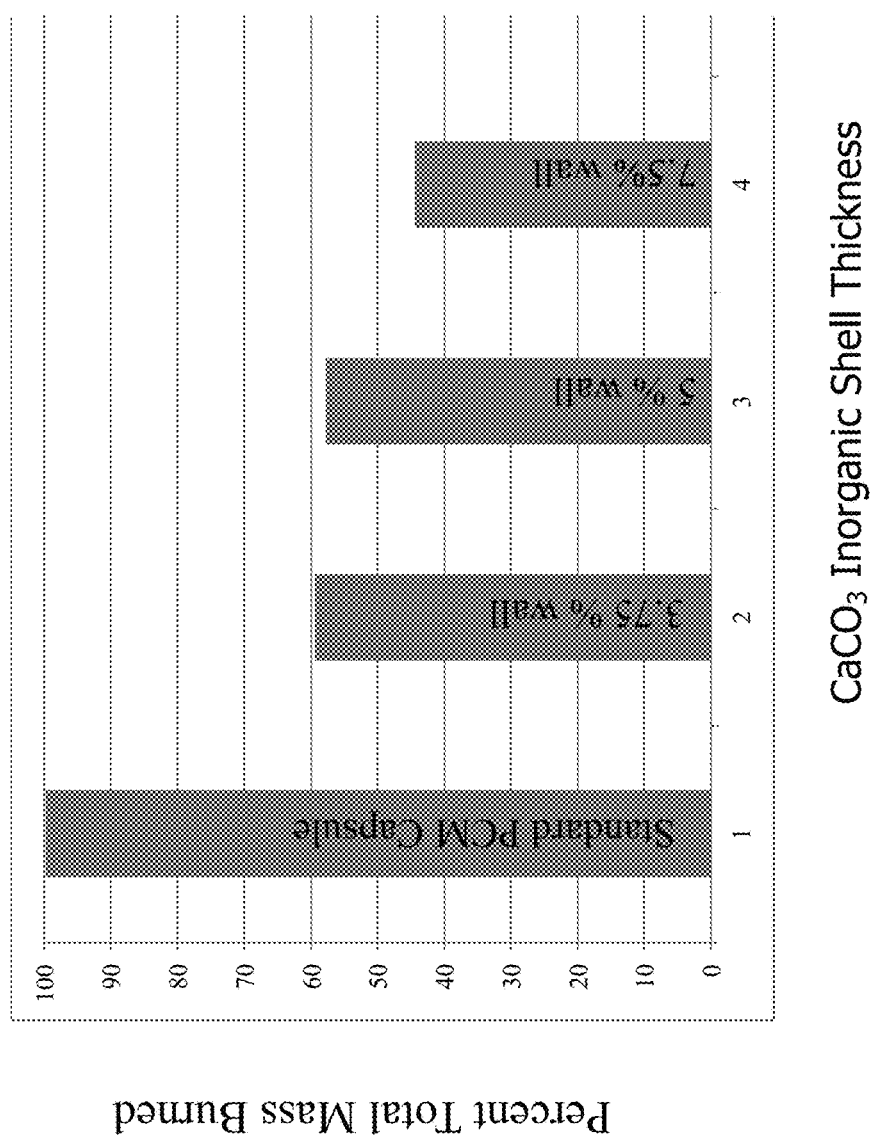

Various inorganic shells comprising calcium and magnesium ions, including the calcium carbonate inorganic shells of FIG. 2, provide the capsules 100c with a flame retardant property as set forth in Working Example 1 and FIG. 7.

Inorganic shells such as calcium sulfate, calcium phosphate, magnesium carbonate, calcium carbonate, and calcium sulfite reduce the percent of total mass burned, compared to microcapsule 100 without an inorganic shell, by at least 16% mass. More particularly, calcium carbonate and calcium sulfite reduced the percent of total mass burned by at least 40%.

Figure 8:
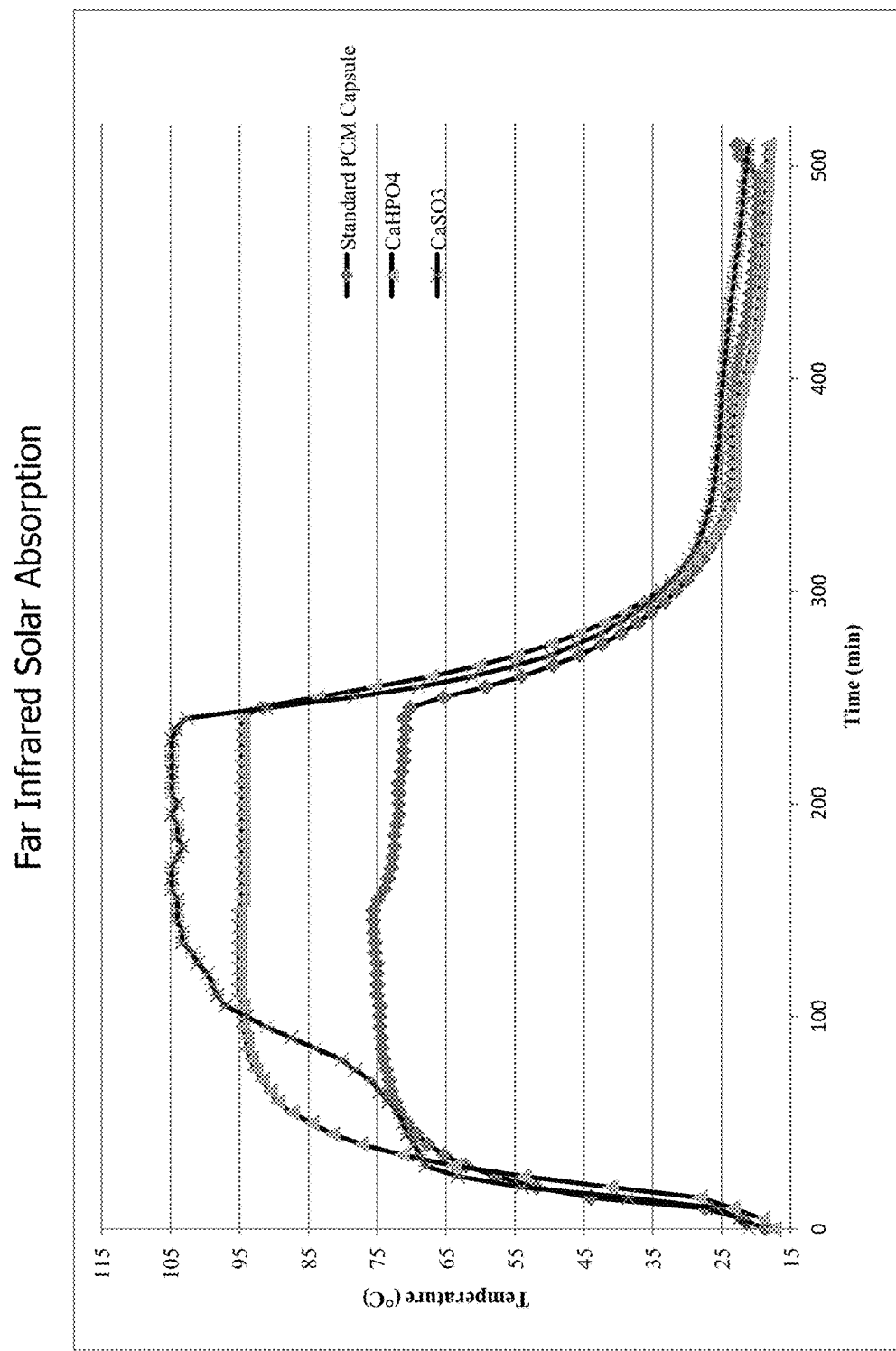
FIG. 8 is a graph of the far infrared solar absorption data for microcapsules having different inorganic shells.
Figure 9:
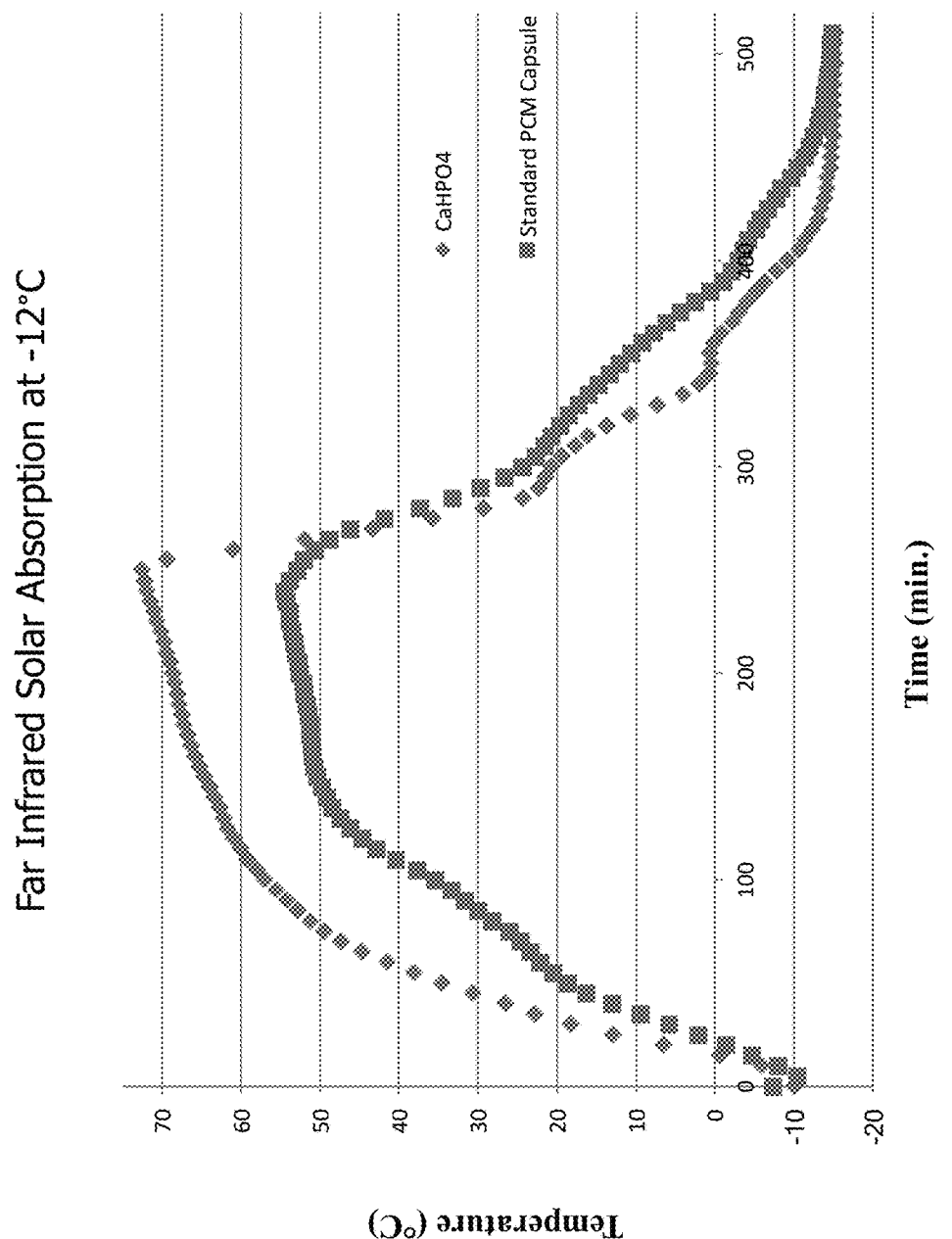
FIG. 9 is a graph of the far infrared solar absorption data at −12° C. for microcapsules having a $CaHPO_4$ inorganic shell.

Some of the inorganic shells comprising calcium ions, such as calcium biphosphate and calcium sulfite, have improved far infrared solar absorption as set forth in Working Example 2 and FIGS. 8 and 9.

Figure 5:
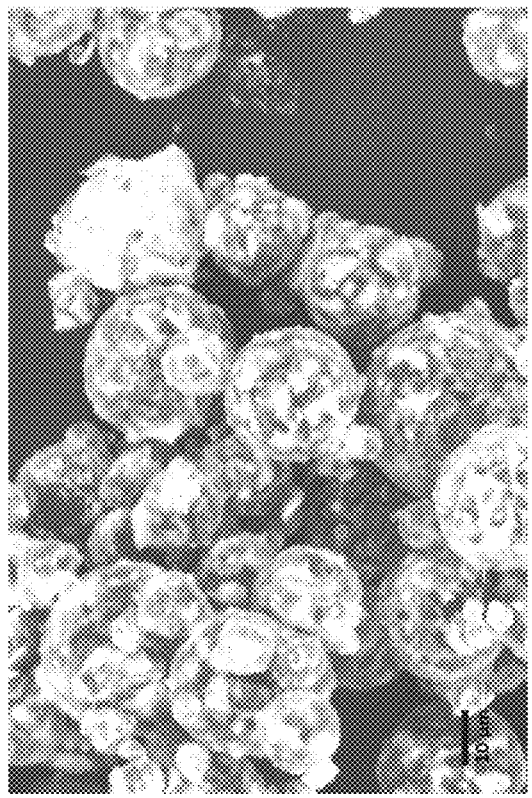
FIGS. 4 and 5 are SEM images, 100 µm and 10 µm respectively, of a plurality of microcapsules having a $Ag_2CO_3$ shell connected to an exterior surface of the polymer wall of a microcapsule of the type shown in FIG. 2.
Figure 4:
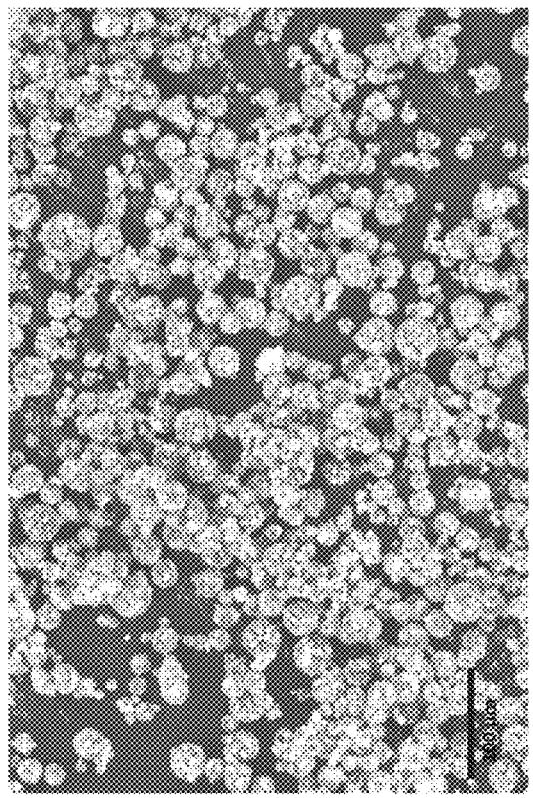

In one embodiment, the capsules 100c have an inorganic shell 106 where the cation 110 is $Ag^+$ and the anion is $CO_3^{-2}$. The silver carbonate inorganic shell formed is a solid that may be continuous or discontinuous about the polymer wall 104. FIGS. 4 and 5 are SEM images of capsules 100c having a discontinuous silver carbonate inorganic shell tethered to the polymer wall 104 of the underlying capsule 100. These capsules 100c, based on their size, are microcapsules having an average particle size of 90 μm, 0.95% free wax, and an enthalpy of 125 J/g. An inorganic shell comprising silver was shown to have antibacterial and antifungal properties as seen in Working Example 3.

Figure 10:
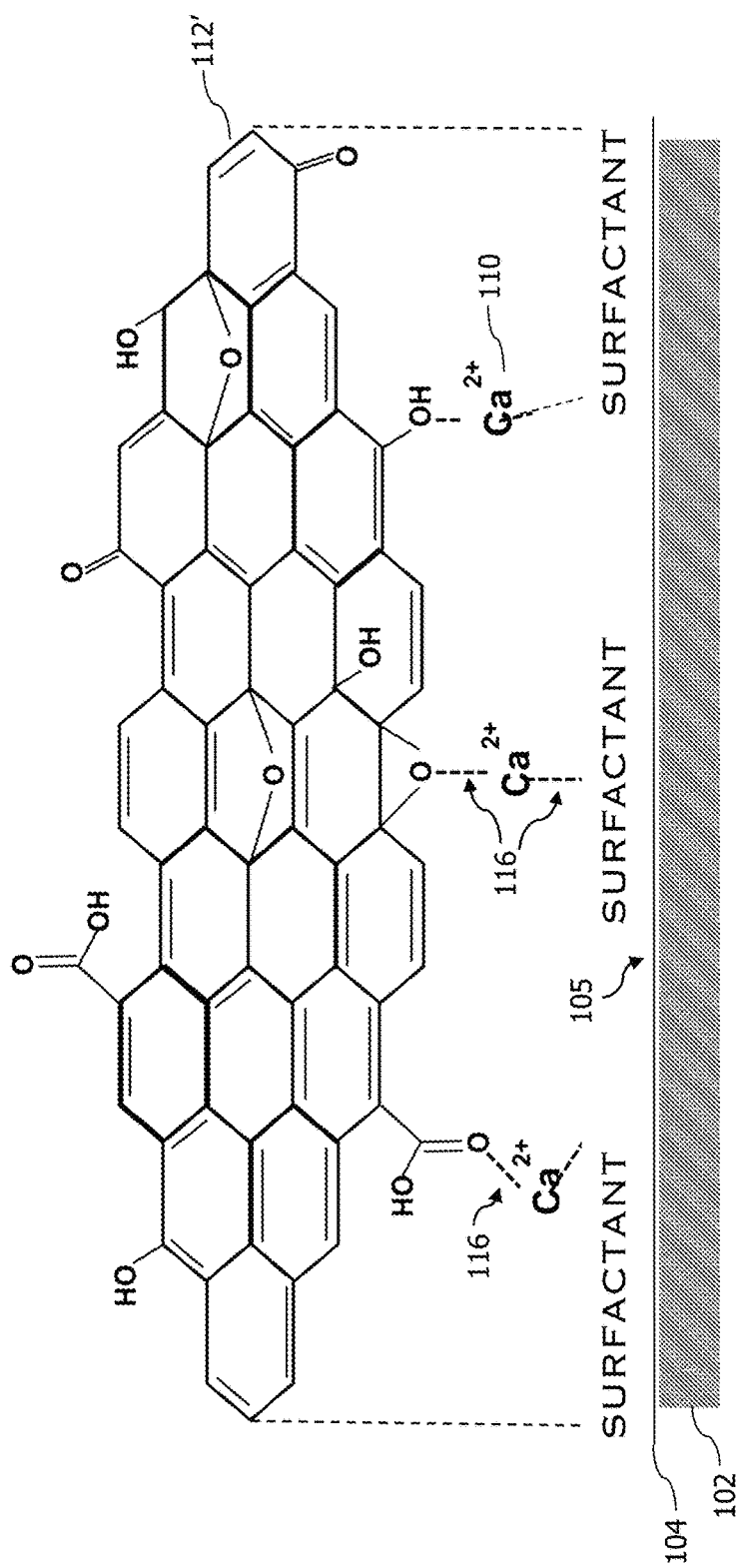
FIG. 10 is an illustration representing the tethering of graphene oxide solid to the exterior surface of a polymer wall of a microcapsule.

In another embodiment, the shell is formed of a plurality of monomeric sheets having a cation selected from one or more of calcium ions, silver ions, and magnesium ions, and graphene oxide as the anion equivalent. Referring to FIG. 10, graphene oxide 112' has epoxide bridges, hydroxyl groups and carboxylic acid functionality that are believed to have electrostatic interaction 116 with the positive charge on the calcium cations 110. The calcium cations 110 bond the graphene oxide sheets 112' to the surfactant tethered to the polymer wall 104 surrounding the core composition 102 and may also be available to bond the graphene oxide sheets to one another. The bulk graphene oxide material is dispersed in neutral to basic solution to yield monomeric sheets during the method of making the capsules 100c.

Graphene has a high thermal conductivity (4840-5300 W/mK), and graphene has been shown to improve thermal conductivity in PCMs. In order to tether graphene to the surface of a PCM capsule, graphene is functionalized with varying oxide groups. As such, the graphene oxide-calcium shell has the ability to improve thermal conductivity of the capsules 100c. To put these capsules to a good use, a label, which may be an adhesive label, was created that includes capsules having the graphene oxide-calcium shell on pre-formed capsules housing a phase change material composition as its core. The label was applied to an electronic device to improve the electronic device's performance. A cell phone was used as the electronic device in Working Example 4, which evidenced an increase of about 10.5% in the speed of running programs and the battery life as monitored using the android application AuTuTu. The device performance was improved by the cooling technology of the PCMs, which is enhanced by the high thermal conductivity in the graphene oxide-calcium shell.

Referring again to FIG. 1, a method for depositing the outer shell 106 onto a polymer wall 104 of an already encapsulated phase change material (PCM), capsule 100, is described. The outer shell 106 is deposited onto the existing polymer wall of microcapsules 100 in an aqueous solution at temperatures between about 20° C. to about 70° C. As discussed above, the polymer wall 104 of microcapsules 100 may be, but are not limited to, organic polymers, cross-linked melamine (CM), and acrylic walls. In preferred embodiments, and those used in the working examples, the average capsule size (diameter) for the pre-formed capsules 100 ranges from about 2 μm to 85 μm. The polymer wall 104 is used as a scaffold in which a surfactant 108 can be applied, where the surfactant 108 tethers the outer shell 106 to the exterior surface 105 of the polymer wall 104. Either ionic or nonionic surfactants can be used, but ionic surfactants are preferred. The surfactant 108 is dissolved in water, typically deionized water, which may be warmed. The pre-formed capsules 100 are added to the surfactant solution (or vice versa) with stirring for sufficient time to allow the surfactant 108 to tether to the polymer wall 104 thereof, thereby forming intermediate PCM capsules 100a.

The surfactant solution typically has a concentration of about 0.5% to about 3% by weight relative to the weight of pre-formed capsules selected for the batch.

After the surfactant 108 is applied to the polymer wall 104, a solution of metal cations 110 ($X^+$) is added dropwise into the aqueous solution of intermediate PCM capsules 100a, preferably with stirring for a sufficient time to allow the cations to be associated/attracted to the surfactant. Before the dropwise addition, a metal compound that is soluble in water was dissolved in water, with heat if appropriate. The metal-containing solution comprised of 0.5% to about 25% by weight, more preferably about 1% to about 11% by weight, metal in deionized water, which was added dropwise to the surfactant coated PCM solution. The metal cations 110 are attracted to the surfactant 108 tethered to the exterior surface of the intermediate PCM capsules 100a, thereby forming secondary intermediate PCM capsules 100b.

In a separate container, the selected anion compound that is soluble in water is dissolved in water, typically with heating. The anion-containing solution is comprised of 0.5% to about 25% by weight, more preferably about 1% to about 13% by weight, metal in deionized water. This solution of anions 112 ($Y^-$) was added dropwise, in a similar manner to the addition of metal cation 110, to the solution of secondary intermediate PCM capsules 100b. The anion 112 must be insoluble in water with the previously added metal cation 112 in order to form a precipitated or deposited solid as a shell 106. After the anion 112 is added to solution, and enough time has been allowed for the shell 106 to form, the solution is filtered and washed several times in deionized water.

The capsules made by the process discussed above can be tailored to have a desired amount of shell material that balances the desired properties provided by the core composition and the shell itself. The shell 106 may comprise about 1% to about 10% by weight of each capsule, more preferably about 3% to about 8% by weight of each capsule.

WORKING EXAMPLES

Example 1

2.5 g of an ionic surfactant, sodium dodecylbenzenesulfonate (SDBS), was dissolved in 400 g of deionized water and heated to 34° C. 50 g of pre-formed organic PCM capsules having a diameter of 20 μm were added to the solution of SDBS with stirring until the surfactant was associated to the exterior surface of the capsule wall, thereby forming intermediate PCM capsules. Separately, 22.2 g of calcium chloride ($CaCl_2$) was dissolved in 600 mL deionized water and heated to 40° C. The $CaCl_2$ solution was added dropwise to the solution of intermediate PCM capsules with stirring until the metal was associated with the surfactant on the surface of the capsules, thereby forming secondary intermediate PCM capsules. In a separate container, 21.2 g of sodium carbonate (Na$_2$CO$_3$) was dissolved in 500 mL of deionized water and heated to 40° C. The Na$_2$CO$_3$ solution was added dropwise to the solution of secondary intermediate PCM capsules. The entire solution was allowed to stir until the precipitation of Ca$_2$CO$_3$ formed the inorganic shell about each pre-formed organic PCM capsule. The product was then filtered and washed several times in deionized water.

Example 2

The procedure of Example 1 was repeated for the following surfactant combinations: SPAN™ 60 sorbitan esters with sodium dodecylbenzenesulfonate (SDBS) and ethylene maleic anhydride (EMA) with sodium dodecylbenzenesulfonate (SDBS) as set forth in Table 1 below.

Example 3

The procedure in Example 1 and the surfactants in Example 2 were repeated using the following metal-anion combinations: CaCO$_3$, CaHPO$_4$, Ca$_3$(PO$_4$)$_2$, Ca(H$_2$PO$_4$)$_2$, CaSO$_4$, CaSO$_3$, Ca(HSO$_4$)$_2$, MgCO$_3$, MgHPO$_4$, Mg$_3$(PO$_4$)$_2$, Mg(H$_2$PO$_4$)$_2$, Ag$_2$CO$_3$, Ag$_3$PO$_4$, Ag$_2$HPO$_4$, AgH$_2$PO$_4$, Ag$_2$SO$_4$, Ag$_2$SO$_3$, and AgHSO$_4$, Cu$_3$(PO$_4$)$_2$, CuHPO$_4$, CuCO$_3$, FeCO$_3$, Fe$_3$(PO$_4$)$_2$, and FeHPO$_4$.

Selected capsules from Example 3, each having about 5% by weight of the identified inorganic shell per capsule, were evaluated for the average particle size, the percent of free wax, the enthalpy value for the capsules, and the temperature at which a 10% weight loss was experienced. The data is presented below in Table 1.

TABLE 1

| Sample | shell/polymer wall | size (μm) | surfactant | free wax | Enthalpy (J/Kg) | 10% wt. loss at T (° C.) |
|---|---|---|---|---|---|---|
| 1 | CaHPO$_4$/CM | 41.3 | SPAN ™ 60/SDBS | 4.61% | 131 | 191 |
| 2 | CaHPO$_4$/CM | 20.7 | SDBS | 0.37% | 143 | 335 |
| 3 | CaHPO$_4$/CM | 39.1 | EMA/SDBS | 0.81% | 125 | 269 |
| 4 | CaHPO$_4$/MF | 74.7 | SDBS | 0.42% | 115.7 | 296 |
| 5 | CaHPO$_4$/Acrylic | 117 | SDBS | 0.17% | 120 | 203 |
| 6 | Ca$_3$(PO$_4$)$_2$/CM | 230 | SPAN ™ 60/SDBS | 7.79% | 142 | 197 |
| 7 | Ca$_3$(PO$_4$)$_2$/CM | 23.7 | SDBS | 1.60% | 119 | 239 |
| 8 | CaCO$_3$/CM | 39.3 | SDBS | 0.31% | 136 | 403 |
| 9 | CaCO$_3$/CM | 32.9 | SPAN ™ 60 & SDBS | 4.70% | 145 | 313 |
| 10 | CaCO$_3$/MF | 22.9 | SDBS | 0.11% | 109 | 382 |
| 11 | CaCO$_3$/Acrylic | 6.72 | SDBS | 0.18% | 136 | 233 |
| 12 | MgCO$_3$/CM | 180 | SPAN ™ 60 & SDBS | 2.04% | 150 | 281 |
| 13 | MgCO$_3$/CM | 142 | SDBS | 0.81% | 154 | 375 |
| 14 | Ag$_2$CO$_3$/CM | 40.3 | SPAN ™ 60 & SDBS | 0.95% | 94 | 340 |
| 15 | CaSO$_4$/CM | 25.5 | SPAN ™ 60/SDBS | 2.58% | 195 | 264 |
| 16 | CaSO$_4$/CM | 32.2 | SDBS | 0.44% | 197 | 395 |
| 17 | Ca(HSO$_4$)$_2$/CM | 30.2 | SPAN ™ 60/SDBS | 4.65% | 182 | 261 |
| 18 | CaSO$_3$/CM | 36.1 | SPAN ™ 60/SDBS | 1.90% | 125 | 281 |
| 19 | CaSO$_3$/CM | 37.2 | SDBS | 0.34% | 149 | 309 |
| 20 | CaSO$_3$/MF | 22.8 | SDBS | 0.31% | 118 | 391 |
| 21 | CaSO$_3$/acrylic | 15.7 | SDBS | 0.21% | 124 | 225 |

Suitable capsules were made ranging from an average particle size of about 7 μm to about 230 μm, having free wax of about 0.1% to about 8%, having enthalpy values from about 94 J/g to about 200 J/g, and 10% weight loss at temperatures from about 191° C. to about 400° C.

Example 4

In another method of tethering an inorganic outer wall to a polymeric inner wall, via electrostatic interaction between inorganic nanoparticles and an organic polymer capsule wall, a surfactant acts as the tether to connect a metal-containing compound to the organic polymer wall. The synthesis of these types of core-polymer wall-shell capsules is quite straight forward, as schematically shown in FIG. 1B. First, 2.5 grams of cetyl trimethylammonium bromide (CTAB) is added to 350 grams of DI water and heated with stirring to 40° C. for 30 minutes. After this, 25 grams of preformed microcapsules as described above are added to the surfactant/water mixture and allowed to stir for 2 hours at 40° C. In a separate beaker, 20 grams of Dispal N (nitric acid capped) boehmite is added to 500 grams of DI water with stirring and heated to 45° C. After stirring the microcapsules and surfactant for 2 hours, the nano-boehmite solution is slowly dripped into the microcapsule solution over about an hour via a separatory funnel. After the addition of the nan-boehmite, the resulting mixture is allowed to stir for 2 hours at 40° C., then cooled to ambient temperature and filtered via vacuum pump and washed several times in DI water.

One application for the capsules with the nano-boehmite tethered to the exterior surface thereof is to provide flame retardant properties to the capsules.

Example 5

Example 4 was repeated using other surfactants and combinations of surfactants disclosed herein as well as other nanomaterials such as titanium dioxide, silicon oxide, zinc oxide, copper oxide, zirconium oxide, and other metal oxide-hydroxide nanoparticles.

Flammability Study

One application of inorganic coated PCMs is reduced flammability. For example, the average house fire burns at around 1100° C., while CaCO$_3$ can withstand temperatures up to 1339° C. before melting. Therefore, coating a PCM in an inorganic material such as CaCO$_3$ should decrease the flammability of the PCM, as the flames would have to burn through the inorganic material first.

The flame retardant properties of capsules having a PCM core composition and a CaCO$_3$ shell tethered to a polymer wall of the capsule by a surfactant were tested and compared to the naked pre-formed capsules. The mean size of the PCMs used in the flammability study were 25 µm in diameter, the core composition comprised octadecane hydrocarbon, and the polymer shell was a crosslinked melamine. Each capsule had an inorganic shell that was about 5% by weight thereof. Samples were first dried on a moisture balance to ensure similar water content in all samples. Then, each sample was placed in a glass petri dish and weighed. The petri dish was then placed in a fume hood, and each sample was lit on fire and allowed to burn to completion. The mass of the remaining sample (if any) after completion of burning was then recorded, and the percentage of the total sample mass burned was calculated.

Figure 6:
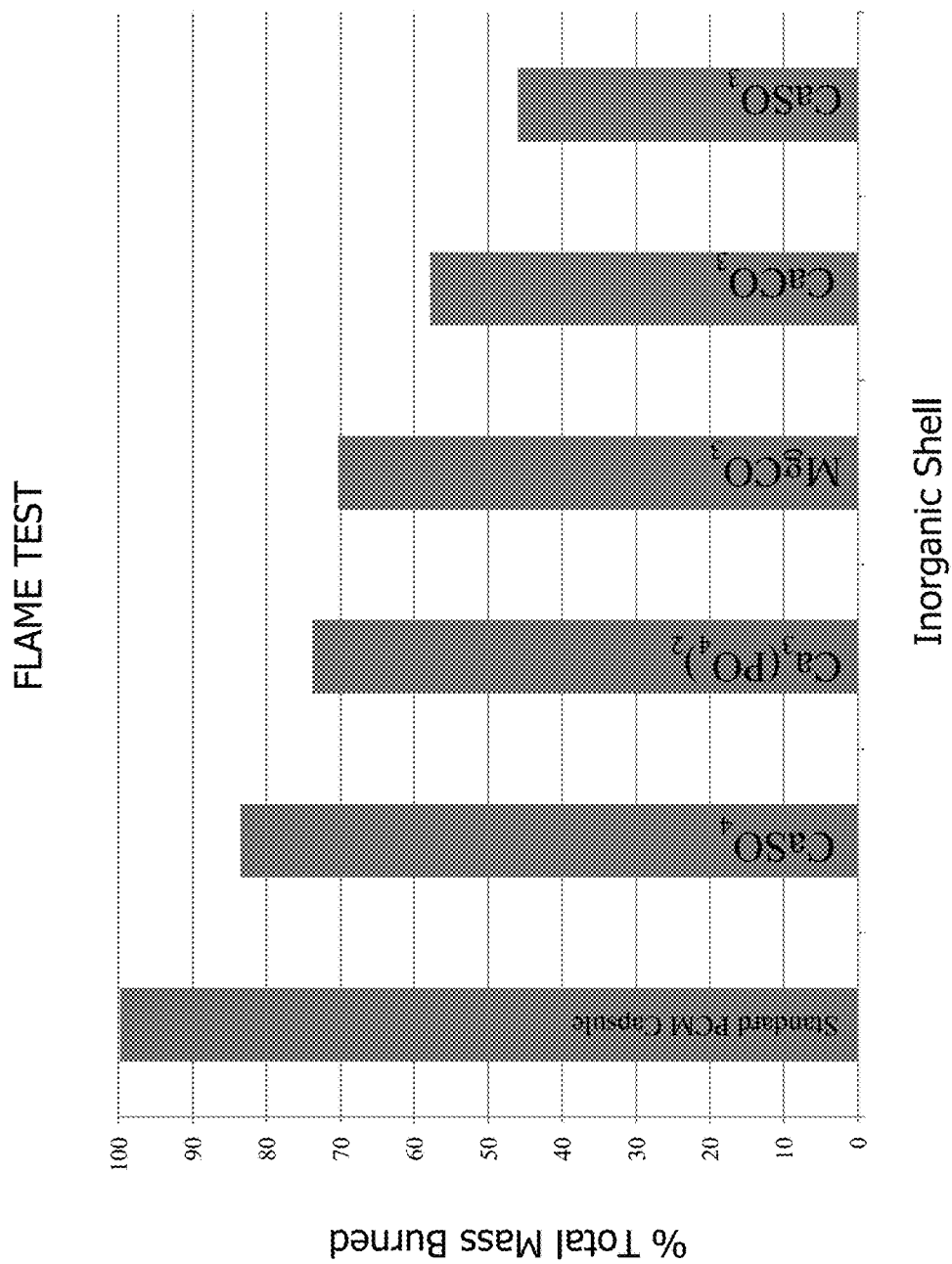
FIGS. 6 and 7 are bar graphs of flame test data for various microcapsules having inorganic shells showing the percent of the total mass burned relative to the inorganic shell material of the microcapsules.

The bar graph in FIG. 6 shows a record of the percent total mass burned of the naked pre-formed "standard" capsule as compared to the pre-formed capsules having the additional inorganic shell. The standard capsule had a total mass loss of 99.7%, PCMs having a $CaSO_4$ shell on a polymeric capsule wall had a mass loss of 83.5%, PCMs having a $Ca_3(PO_4)_2$ shell on a polymeric capsule wall had a mass loss of 73.8%, PCMs having a $MgCO_3$ shell on a polymeric capsule wall had a mass loss of 70.3%, PCMs having a $CaCO_3$ shell on a polymeric capsule wall had a mass loss of 57.8%, and PCMs having a $CaSO_3$ shell on a polymeric capsule wall had a mass loss of 46.0% after burning. The data shows that the addition of the inorganic shell to the pre-formed capsules improves the flame retardant properties thereof.

The flammability of the PCMs is also dependent on the amount of inorganic material defining the inorganic shell on a polymeric capsule wall. As shown in the bar graph of FIG. 7, the naked pre-formed "standard" capsule (mean size 25 µm) had a total mass loss of 99.7%, but the addition of a 3.75% by weight inorganic shell comprising $CaCO_3$ allows only 59.5% of the mass of the sample to burn, a 5% by weight inorganic shell of $CaCO_3$ allows only 57.5% of the mass of the sample to burn, and a 7.5% by weight inorganic shell of $CaCO_3$ allows only 44.4% of the mass of the sample to burn. Furthermore, the same experiment was run with a smaller 10 µm average diameter capsule, which means the same amount of the inorganic material for the inorganic shell has a larger surface area. Here, only 41.8% of the sample burned for capsules having 7.5% by weight inorganic shell of $CaCO_3$, compared to the 44.4% noted above. This demonstrates that a larger surface area covered (i.e., the small capsules) allows for slightly better inorganic wall coverage and has slightly higher flame retardant properties.

Fir Absorption Study

Another application of inorganic coated PCMs is to absorb far infrared (FIR) light from the sun for use in solar energy storage. Energy is released in the form of FIR light from the sun, and radiates both during daytime and nighttime. Because inorganic compounds containing P—O and S—O bonds have high absorption in the FIR region, an inorganic wall containing such bonds would further PCM applications in solar energy storage.

A demonstration of the inorganic wall's ability to absorb far infrared light was conducted by placing samples under a far infrared light for 4 hours, which emitted light from 5-25 µm. The temperature of each sample was recorded for 8 hours using a thermometer attached to a temperature probe, which was inserted into a sample. The temperature was monitored during this 8 hour period as follows: 4 hours with the light on; and 4 hours after the light was turned off, thereby mimicking daytime and nighttime. The higher the temperature of the sample over time, the better the FIR absorption.

FIG. 8 shows that the naked pre-formed "standard" capsule (mean size 25 µm) increased in temperature up to 75° C. while the light was on, and then returned to room temperature after 3 hours. 25 µm capsules with an octadecane core, melamine-formaldehyde wall, and a 5% by weight inorganic coating ($CaSO_3$ and $CaHPO_4$), made according to Example 3, reached temperatures of 105° C. and 95° C., respectively, and decreased to room temperature after almost 4 hours, demonstrating a higher storage capability under FIR light.

To ensure that the heat in the room was not contributing to the FIR absorption, further FIR absorption experiments were carried out in a −12° C. freezer. FIG. 9 shows that the same naked pre-formed "standard" capsule increased in temperature up to 55° C. while the light was on, and then returned to −12° C. after 3 hours. Inorganic coated ($CaHPO_4$) capsules reached 73° C. temperatures, and decreased to −12° C. after almost 4 hours, demonstrating a higher storage capability under FIR light even in cold conditions.

Antibacterial Study

Currently, biocides are added to a PCM capsule slurry before it is filtered in order to decrease any bacterial growth. However, there is still room for improvement. Some metals such as silver and copper are known antibacterials; therefore, naked pre-formed "standard" capsules (mean size 25 µm) were coated with $Ag_2CO_3$ according to the procedure of Example 3 above and were challenged with bacterial and fungal colonies. In this study, it was found that the addition of the $Ag_2CO_3$ shell to the standard capsules showed no bacterial recovery, which demonstrates that the PCM having the inorganic shell has a higher antibacterial resistance than a biocide treated PCM capsule.

The study was conducted according to ASTM D 2547-06 against four bacteria and 1 fungus based on a historical data of growth on the naked pre-formed "standard" capsules treated with a biocide. The four bacteria were: *Stenotrophomonas maltophilia; Burkholderia cepacia, Providencia rettgeri*, and *Sphingomonas paucimobilis*. The fungus was *Penicillium* spp. Each test sample (No. 5 in Table 2) was provided as a slurry comprising 25% by weight of capsules having the $Ag_2CO_3$ shell (no other biocide present). Each slurry was sampled for native bacteria prior to testing. These samples were compared against (No. 1) untreated (no biocide) naked pre-formed "standard" capsules, (No. 2) the standard capsules with 1.6 mL of PROXEL® BN (2000 ppm) biocide, (No. 3) the standard capsules with 2 mL of VANTOCIL® D3 (2500 ppm) biocide, and (No. 4) standard capsules treated with 0.8 mL of PROXEL® BN (1000 ppm) biocide and 1.0 mL of VANTOCIL® IB (1250 ppm) biocide.

100 gram aliquots of each sample were dispensed into sterile containers and inoculated with 0.1 mL, one each, of the organisms and incubated at about 30° C. for one week. Checks for bacterial recovery were done after 1, 2, 5, and 7 days by streaking the sample onto Tryptic soy agar (for the bacteria) and potato dextrose agar (for the fungus) plates. These plates were incubated at 30° C. for one week with growth checks done at 48 hours and 7 days. Then, after week 1, the samples were re-inoculated with 1.0 mL of freshly prepared bacterial broths and fungal spore suspension, respectively. Checks for bacterial recovery were performed after 8, 9, 12, and 14 days according to the same procedure during week 1.

Table 2 below has data from week 1 and week 2. The ratings are as follows: 0 means no bacterial recovery (the best result); 1 means trace contamination (1 to 9 colonies); 2 means light contamination (10 to 99 colonies); 3 means moderate contamination (>100 distinct colonies); and 4 means heavy contamination.

TABLE 2

| Sample | Day 0 | Day 1 24-48 Hour | Day 1 7 Day | Day 2 24-48 Hour | Day 2 7 Day | Day 5 24-48 Hour | Day 5 7 Day | Day 7 24-48 Hour | Day 7 7 Day |
|---|---|---|---|---|---|---|---|---|---|
| Week 1 Results | | | | | | | | | |
| #1 Untreated-TSA | Inoculate | 4 | 4 | 4 | 4 | 2 | 3 | 2 | 3 |
| #1 Untreated-PDA | | 4 | 4 | 4 | 4 | 2 | 3 | 2 | 3 |
| #2 Proxel BN-TSA | | 0 | 0 | 0 | 0 | 0 | 0 | 0 | 0 |
| #2 Proxel BN-PDA | | 0 | 0 | 0 | 0 | 0 | 0 | 0 | 0 |
| #3 Vanticil IB-TSA | | 4 | 4 | 4 | 4 | 1 | 2 | 1 | 2 |
| #3 Vanticil IB-PDA | | 4 | 4 | 4 | 4 | 2 | 2 | 2 | 2 |
| #4 Proxel/Vanticil mix TSA | | 0 | 0 | 0 | 0 | 0 | 0 | 0 | 0 |
| #4 Proxel/Vanticil mix PDA | | 0 | 0 | 0 | 0 | 0 | 0 | 0 | 0 |
| #5 Silver slurry-TSA | | 0 | 0 | 0 | 0 | 0 | 0 | 0 | 0 |
| #5 Silver slurry PDA | | 0 | 0 | 0 | 0 | 0 | 0 | 0 | 0 |
| Week 2 Results | | | | | | | | | |
| #1 Untreated-TSA | Inoculate | 4 | 4 | 3 | 4 | 3 | 4 | 3 | 3 |
| #1 Untreated-PDA | | 4 | 4 | 3 | 4 | 3 | 4 | 3 | 3 |
| #2 Proxel BN-TSA | | 4 | 4 | 1 | 1 | 0 | 0 | 0 | 0 |
| #2 Proxel BN-PDA | | 0 | 0 | 0 | 0 | 0 | 0 | 0 | 0 |
| #3 Vanticil IB-TSA | | 4 | 4 | 2 | 4 | 2 | 3 | 2 | 2 |
| #3 Vanticil IB-PDA | | 4 | 4 | 4 | 4 | 3 | 4 | 2 | 2 |
| #4 Proxel/Vanticil mix TSA | | 1 | 2 | 1 | 1 | 0 | 0 | 0 | 0 |
| #4 Proxel/Vanticil mix PDA | | 1 | 1 | 1 | 1 | 0 | 0 | 0 | 0 |
| #5 Silver slurry-TSA | | 0 | 0 | 0 | 0 | 0 | 0 | 0 | 0 |
| #5 Silver slurry PDA | | 0 | 0 | 0 | 0 | 0 | 0 | 0 | 0 |

As seen from the data above, sample 5 comprising the capsules having a silver carbonate shell performed the best under all conditions over the two week period, even showing no bacterial or fungal growth after addition of 1.0 mL of organisms after week one. The commercially available biocides PROXEL® and VANTOCIL® were not as effective at preventing growth compared to the PCM having the inorganic silver-containing shell.

These capsules are useful, for example, in textiles for health care workers, paints and coatings applications for hospitals, and clean room day care centers. Examples of textiles incorporating microcapsules housing PCMs and teaching how to include the capsules therein include U.S. Pat. Nos. 6,207,738, 6,514,362, 6,503,976, and articles S. Mondal, Applied Thermal Engineering, Volume 28, Issues 11-12, August 2008, pp. 1536-1550, and G. Nelson, International Journal of Pharmaceutics, Volume 242, Issues 1-2, Aug. 21, 2002, pp. 55-62. Examples of paints and coatings incorporating microcapsules housing PCMs include U.S. Pat. Nos. 7,377,968 and 7,938,897, which teach one of skill in the art how to incorporate microcapsules into a paint or coating.

Example 6

2.5 grams of an ionic surfactant, such as sodium dodecylbenzenesulfonate (SDBS), were dissolved in 300 g of deionized water and heated to 34° C. with stirring. 25 grams of pre-formed standard capsules, as a wet cake, having a diameter of 20 μm were added to this solution and allowed to stir until the surfactant was associated to the surface of the capsule wall, about 1 to 2 hours, thereby forming first intermediate capsules. For this example, the pre-formed standard capsules had an octadecane PCM core and a cross-linked melamine polymer wall. Separately, 5.5 grams of calcium chloride ($CaCl_2$) were dissolved in 350 grams of deionized water and heated to 34° C. This solution was then added dropwise to the solution containing the first intermediate capsules and allowed to stir until the metal was associated with (chemically attracted/bonded to) the surfactant on the surface of the pre-formed capsules, about 1 to 2 hours, thereby forming second intermediate capsules. In a separate container, 25 grams of a 5 g/L graphene oxide aqueous solution was mixed with deionized water and heated to 34° C. This solution was then added dropwise to the solution containing the second intermediate capsules. The entire solution was allowed to stir until the graphene oxide was associated chemically attracted/bonded) to the surface of the capsules, about 1 to 3 hours, via chemical attractions/bonds with the $Ca^{2+}$ ions as shown in FIG. 10. The resultant capsules were filtered and washed several times in deionized water, and subsequently tested for size, amount of free wax, enthalpy, a change in the phase transition temperature, the temperature at which 10% weight loss is reached, and the thermal conductivity.

From the data presented in Table 3 below, it can be seen that both the capsules coated in graphene oxide and the capsules with no additional coating have low free core, high enthalpies and high thermal stability. The only major difference is the thermal conductivity. The capsules without graphene oxide (Sample A) have a thermal conductivity of 0.599 W/mK and the capsules with the graphene oxide coating (Sample B) have a thermal conductivity of 0.845 W/mK. The graphene oxide containing capsules have 4% graphene oxide, which was calculated by the loss in enthalpy of the capsules with graphene oxide verses the capsules without graphene oxide coating. Thermal conductivity measurements were taken at temperatures between 22-24° C. via guarded hot plate technique.

TABLE 3

| Sample | Size (μm) | Free wax | Enthalpy (J/g) | ΔMP-FP (° C.) | 10% wt. loss (° C.) | Thermal conductivity (W/mK) |
|---|---|---|---|---|---|---|
| A (control) | 52.7 | 0.46% | 182 | 8.54 | 386.7 | 0.599 |
| B (graphene oxide shell) | 57.9 | 0.69% | 175 | 8.74 | 387 | 0.845 |

Study of Thermal Conductivity on Electronic Devices

Another application of the inorganic coated PCMs disclosed herein is as a cooling product for electronic devices.

For example, electronic devices, such as cell phones, are becoming thinner and smaller, and, with this, have the potential to conjure large amounts of heat. PCMs have applications as heat sinks due to their large heat of fusion, which could improve the thermal performance of electronic devices, and graphene oxide is known to have a large thermal conductivity, which could aid in the PCM's performance with respect to electronic devices. One option to incorporate graphene is to disperse the graphene into the organic core of the PCM; however, this has proven to have dispersion issues.

Here, graphene oxide, an anion equivalent, is deposited onto the outer surface of a polymer wall of a pre-formed standard capsule, by the methods disclosed above. In particular, capsules having a graphene oxide-Ca shell made according to Example 4 were incorporated into a cooling sticker as follows: a solution of a binder, dispersing agent and the graphene-oxide-Ca shelled capsules was coated onto a foil substrate having a pressure sensitive adhesive on the opposing side thereof using an 8-path wet film applicator. The solution was allowed to dry.

The solution was made by mixing the binder and the graphene oxide-Ca shelled capsules in a 1:0.865 ratio and adding a few drops of the dispersing agent to reduce agglomeration of the capsules. The binder used was Joncryl® 624 acrylic polymer emulsion and the dispersing agent was a 2 g/L SDBS aqueous solution.

The cooling sticker was adhered to a cell phone, and the speed of running programs and the battery life were monitored. The android application AuTuTu was used to benchmark performance with and without the label. The cell phone with the cooling sticker containing the graphene oxide-Ca shell performed better than the cell phone without a cooling sticker. First, graphene oxide was mixed into a paste mixture with MF PCM capsules and a binder as a control. The total graphene oxide content of this was about 3% by mass. The average increase in device performance during this control test was found to be 10.66%. Next, graphene oxide-Ca was coated onto the surface of MF PCM capsules; then coated capsules were mixed with the binder. The total graphene oxide content of this was about 0.8% by mass. The average increase in device performance using graphene oxide-Ca coated capsules was found to be 11.4%. This demonstrates that applying graphene oxide to the surface of capsules improves device performance even when using 25% less graphene oxide material, which is much more cost effective.

As is evident from the numerous studies conducted on the resultant capsules, various inorganic shells add different beneficial properties to the capsules. The properties depend on the choice of solid for the shell and the thickness (amount) of the solid deposited to form the shell. For example, a thicker shell will result in a lower overall enthalpy for the capsules, which at some threshold becomes too low for the capsules' purpose. Thus, the enthalpy value of the capsules, from the presence of the phase change material in the core of the capsule, must be balanced against the choice and amount of shell material deposited on the capsule. As seen from the studies above, the choice of the material for the shell can affect the FIR absorption properties, the flame retardant properties, antibacterial properties, and thermal conductivity, and even combinations thereof.

Moreover, because the shell material is not directly encapsulating the core material, the capsules have the advantage of minimizing leakage of the core material, while retaining the flame retardant, FIR absorption, antibacterial and antifungal, and higher thermally conductive properties. Moreover, because the core material is directly encapsulated by polymeric material and indirectly encapsulated by inorganic material, the capsules have the advantage of minimizing leakage of the core material, while retaining the flame retardant, FIR absorption, antibacterial and antifungal, and higher thermally conductive properties.

The embodiments of this invention shown in the drawings and described above are exemplary of numerous embodiments that may be made within the scope of the appended claims. It is contemplated that numerous other configurations of microcapsules may be created by taking advantage of the disclosed two-stage polymerization method of making the microcapsules. In short, it is the Applicants' intention that the scope of the patent issuing herefrom be limited only by the scope of the appended claims.

What is claimed is:

1. A capsule comprising:
   a pre-formed capsule comprising a core composition encapsulated within a polymer wall; and
   an inorganic shell connected to an exterior surface of the polymer wall of the pre-formed capsule by a surfactant, the inorganic shell comprising: (i) a cation attracted to the surfactant and an anion, graphene oxide, an amine, or a carboxylate chemically bonded to the cation; or (ii) a metal-containing compound attracted to the surfactant;
   wherein the surfactant comprises an ionic surfactant.

2. The capsule of claim 1, wherein the core comprises a phase change material.

3. The capsule of claim 1, wherein the cation is selected from the group consisting of calcium ions, silver ions, magnesium ions, iron ions, copper ions, and cobalt ions, and combinations thereof.

4. The capsule of claim 3, wherein the cation is a silver ion, and the inorganic shell has antibacterial and antifungal growth properties.

5. The capsule of claim 3, wherein the inorganic shell provides the capsule with a flame retardant property that reduces the percent of total mass burned, compared to the capsule without the shell, by at least 16% mass.

6. The capsule of claim 5, wherein the inorganic shell reduces the percent of total mass burned by at least 40%.

7. The capsule of claim 2, wherein the full or partial inorganic shell comprises a cation and an anion, and is selected from the group consisting of $CO_3^{-2}$, $HPO_4^{-2}$, $PO_4^{-3}$, $SO_4^{-2}$, $SO_3^{-2}$, $OH^{-1}$, $HSO_4^{-1}$, and combinations thereof.

8. The capsule of claim 7, wherein the anion of the inorganic shell comprises $HPO_4^{-2}$, $PO_4^{-3}$, $SO_4^{-2}$, $SO_3^{-2}$, $HSO_4^{-1}$ or combinations thereof.

9. The capsule of claim 1, wherein the inorganic shell comprises a discontinuous wall encapsulating the polymer wall.

10. The capsule of claim 1, wherein the inorganic shell comprises a cation and graphene oxide.

11. The capsule of claim 10, wherein the cation comprises calcium ions and the core comprises a phase change material.

12. The capsule of claim 10, wherein the inorganic shell comprises a discontinuous wall encapsulating the polymer wall.

13. The capsule of claim 1, wherein the inorganic shell comprises the metal-containing compound attracted to the surfactant, the metal-containing compound being a metal oxide or a metal oxide-hydroxide.

14. The capsule of claim 1, wherein the polymer wall comprises melamine formaldehyde, gelatin, cross-linked melamine, resorcinol urea formaldehyde, or acrylic polymer.

15. The capsule of claim 13, wherein the polymer wall comprises a cross-linked melamine and the core comprises a phase change material, the cross-linked melamine comprising melamine formaldehyde polymerized with a crosslinking agent comprising:
(a) a reaction product of a cyclic urea (U) and a multifunctional aldehyde (A), and
(b) at least one crosslinker selected from the group consisting of
(b1) reaction products of an aminotriazine and at least one aldehyde selected from the group consisting of aliphatic monoaldehydes and multifunctional aliphatic aldehydes having the structure $Y(CHO)_n$, where Y is an n-functional aliphatic residue, and n is greater than 1, where U is not dihydroxyethylene urea if the crosslinker (b) is (b1),
(b2) reaction products of urea and/or cyclic ureas and formaldehyde,
(b3) alkoxycarbonylaminotriazines,
(b4) multifunctional isocyanates which may be partially or completely blocked,
(b5) reaction products of phenols and aliphatic monoaldehydes,
(b6) multifunctional epoxides,
(b7) multifunctional aziridines,
(b8) multifunctional carbodiimides,
wherein any of the crosslinkers (a) and (b) which have hydroxyl groups may be etherified with one or more linear, branched, or cyclic aliphatic alcohols.

16. A method for surface treating capsules, the method comprising:
providing pre-formed capsules comprising a core composition encapsulated within a polymer wall;
mixing an aqueous surfactant comprising an ionic surfactant and the pre-formed capsules together, wherein the surfactant attaches to an exterior surface of the polymer wall to form a surfactant-capsule intermediate;
firstly adding aqueous cations to the surfactant-capsule intermediate to form secondary intermediate capsules with the cations associated with the surfactant or adding a metal-containing compound suspended, solubilized, or dissolved in water to the surfactant-capsule intermediate to form an inorganic solid as an outer shell of the capsules; and
when the secondary intermediate capsules are formed, secondly adding aqueous anions, graphene oxide, an amine, or a carboxylate to the secondary intermediate capsules to chemically bond to the cation and form an inorganic solid as an outer shell of the capsules.

17. The method of claim 16, further comprising forming the capsules before mixing with the aqueous surfactant.

18. The method of claim 16, wherein the shell is a discontinuous outer shell.

19. The method of claim 16, wherein the core comprises a phase change material.

20. The method of claim 19, wherein the cation is selected from the group consisting of calcium ions, silver ions, magnesium ions, and combinations thereof.

21. The method of claim 19, wherein the shell comprises a cation and an anion, selected from the group consisting of $CO_3^{-2}$, $HPO_4^{-2}$, $PO_4^{-3}$, $SO_4^{-2}$, $SO_3^{-2}$, $OH^{-1}$, $HSO_4^{-1}$, and combinations thereof.

22. The method of claim 16, wherein the shell comprises a cation and an anion equivalent, wherein the anion equivalent is graphene oxide.

23. The method of claim 16, wherein the metal-containing compound was added during the adding step, the metal-containing compound being a metal oxide or a metal oxide-hydroxide.

24. The method of claim 16, wherein the polymer wall comprises melamine formaldehyde, gelatin, cross-linked melamine, resorcinol urea formaldehyde, or acrylic polymer.

25. An article of manufacture comprising:
a capsule incorporated therein, the capsule comprising:
a pre-formed capsule comprising a core composition encapsulated within a polymer wall; and
an inorganic shell connected to an exterior surface of the polymer wall of the pre-formed capsule by a surfactant, the inorganic shell comprising: (i) a cation attracted to the surfactant and an anion, graphene oxide, an amine, or a carboxylate chemically bonded to the cation; or (ii) a metal-containing compound attracted to the surfactant;
wherein the surfactant comprises an ionic surfactant.

26. The article of manufacture of claim 25, wherein the inorganic shell comprises a cation and graphene oxide.

27. The article of manufacture of claim 26, wherein the article of manufacture is a cooling apparatus for an electronic device comprising a substrate with a coating applied thereto that comprises a plurality of the capsules dispersed therein.

28. The article of manufacture of claim 27, wherein the substrate includes an adhesive layer on the substrate on a surface opposite the coating, and the inorganic shell comprises at least 1 g of graphene per microcapsule, and the microcapsules increase the average performance of the electronic device by at least 10%.

29. The article of manufacture of claim 25, wherein the core comprises a phase change material, and the cation is selected from the group consisting of calcium ions, silver ions, magnesium ions, iron ions, copper ions, and cobalt ions, and combinations thereof; wherein the capsule has a flame retardant property that reduces the percent of total mass burned, compared to the capsule without the shell, by at least 16% mass.

30. The article of manufacture of claim 29, wherein the inorganic shell reduces the percent of total mass burned by at least 40%.

31. The article of manufacture of claim 29, wherein the article of manufacture is a building material.

32. The article of manufacture of claim 25, wherein the article of manufacture is a solar cell, and the core comprises a phase change material, and the inorganic shell comprises the cation and the anion is selected from the group consisting of $HPO_4^{-2}$, $PO_4^{-3}$, $SO_4^{-2}$, $SO_3^{-2}$, $HSO_4^{-1}$, and combinations thereof.

33. The article of manufacture of claim 25, wherein the article of manufacture is a textile fabric or textile material; wherein the cation is a silver ion, and the inorganic shell has antibacterial and antifungal growth properties.

34. A composition of matter comprising:
a plurality of capsules dispersed with a spreadable medium, the plurality of capsules comprising:
a pre-formed capsule comprising a core composition encapsulated within a polymer wall; and
an inorganic shell connected to an exterior surface of the polymer wall of the pre-formed capsule by a surfactant, the inorganic shell comprising: (i) a cation attracted to the surfactant and an anion, graphene oxide, an amine, or a carboxylate chemically bonded to the cation; or (ii) a metal-containing compound attracted to the surfactant;

wherein the surfactant comprises an ionic surfactant.

35. The composition of matter of claim 34, wherein the cation is a silver ion, and the inorganic shell has antibacterial and antifungal growth properties.

36. The composition of matter of claim 34, wherein the spreadable medium is a paint, or a coating.

\* \* \* \* \*